United States Patent
Riley et al.

(10) Patent No.: US 9,238,151 B2
(45) Date of Patent: *Jan. 19, 2016

(54) DYNAMIC/ADAPTIVE TREATMENT PLANNING FOR RADIATION THERAPY

(71) Applicant: Varian Medical Systems, Inc., Palo Alto, CA (US)

(72) Inventors: James K. Riley, Kirkland, WA (US); Eric Meier, Bellevue, WA (US); J. Nelson Wright, Mercer Island, WA (US); Steven C. Dimmer, Bellevue, WA (US); Timothy P. Mate, Bellevue, WA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 13/888,288

(22) Filed: May 6, 2013

(65) Prior Publication Data

US 2014/0093049 A1    Apr. 3, 2014

Related U.S. Application Data

(63) Continuation of application No. 11/189,431, filed on Jul. 25, 2005, now Pat. No. 8,437,449.

(60) Provisional application No. 60/590,503, filed on Jul. 23, 2004.

(51) Int. Cl.
*A61N 5/10* (2006.01)

(52) U.S. Cl.
CPC .............. *A61N 5/1038* (2013.01); *A61N 5/103* (2013.01); *A61N 5/1048* (2013.01)

(58) Field of Classification Search
CPC ... A61N 5/103; A61N 5/1031; A61N 5/1037; A61N 5/1038; A61N 5/1042; A61N 5/1045; A61N 5/1048; A61N 5/1049; A61N 5/1064; A61N 5/1065; A61N 5/1067; A61N 5/1071; A61N 5/1072; A61N 2005/1061
USPC ................... 378/65, 205, 901; 600/407, 408, 600/425–429
See application file for complete search history.

(56) References Cited

U.S. PATENT DOCUMENTS

| | | | |
|---|---|---|---|
| 3,967,161 A | 6/1976 | Lichtblau | |
| 4,023,167 A | 5/1977 | Wahlstrom | |

(Continued)

FOREIGN PATENT DOCUMENTS

| | | |
|---|---|---|
| JP | 07-313515 | 12/1995 |
| JP | 8166446 | 6/1996 |

(Continued)

OTHER PUBLICATIONS

P.G. Seiler, et al., A novel tracking technique for the continuous precise measurement of tumour positions in confomral therapy, Jun. 7, 2000, IOP Publishing Ltd., Phys. Med. Biol., vol. 45, pp. N103-N110.

(Continued)

*Primary Examiner* — Anastasia Midkiff
(74) *Attorney, Agent, or Firm* — Perkins Coie LLP

(57) ABSTRACT

A facility for facilitating custom radiation treatment planning is described. During a distinguished radiation treatment session for a patient, the facility collects data indicating positioning of a predefined treatment site of the patient relative to a target treatment location throughout the distinguished radiation treatment session. The facility associates the collected positioning data with data describing one or more other aspects of the distinguished radiation treatment session. The facility provides the associated data to a treatment planning facility to determine a treatment plan for future radiation treatment sessions for the patient.

20 Claims, 14 Drawing Sheets

(56) References Cited

U.S. PATENT DOCUMENTS

| | | |
|---|---|---|
| 4,114,601 A | 9/1978 | Abels |
| 4,123,749 A | 10/1978 | Hartmann et al. |
| 4,127,110 A | 11/1978 | Bullara |
| 4,160,971 A | 7/1979 | Jones et al. |
| 4,222,374 A | 9/1980 | Sampson et al. |
| 4,260,990 A | 4/1981 | Lichtblau |
| 4,393,872 A | 7/1983 | Reznik et al. |
| 4,618,822 A | 10/1986 | Hansen |
| 4,633,250 A | 12/1986 | Anderson, III et al. |
| 4,643,196 A | 2/1987 | Tanaka et al. |
| 4,696,287 A | 9/1987 | Hortmann et al. |
| 4,795,995 A | 1/1989 | Eccleston et al. |
| 4,799,495 A | 1/1989 | Hawkins et al. |
| 4,909,789 A | 3/1990 | Taguchi et al. |
| 4,936,823 A | 6/1990 | Colvin et al. |
| 4,945,914 A | 8/1990 | Allen |
| 4,994,079 A | 2/1991 | Genese et al. |
| 5,031,634 A | 7/1991 | Simon |
| 5,062,847 A | 11/1991 | Barnes |
| 5,095,224 A | 3/1992 | Renger |
| 5,099,845 A | 3/1992 | Besz et al. |
| 5,107,862 A | 4/1992 | Fabian et al. |
| 5,142,292 A | 8/1992 | Chang |
| 5,170,055 A | 12/1992 | Carroll et al. |
| 5,325,873 A | 7/1994 | Hirschi et al. |
| 5,353,804 A | 10/1994 | Kornberg et al. |
| 5,409,004 A | 4/1995 | Sloan |
| 5,423,334 A | 6/1995 | Jordan |
| 5,425,367 A | 6/1995 | Shapiro et al. |
| 5,425,382 A | 6/1995 | Golden et al. |
| 5,446,548 A | 8/1995 | Gerig et al. |
| 5,509,900 A | 4/1996 | Kirkman |
| 5,528,651 A | 6/1996 | Leksell et al. |
| 5,626,630 A | 5/1997 | Markowitz et al. |
| 5,638,819 A | 6/1997 | Manwaring et al. |
| 5,651,043 A | 7/1997 | Tsuyuki et al. |
| 5,680,106 A | 10/1997 | Schrott et al. |
| 5,697,384 A | 12/1997 | Miyawaki et al. |
| 5,707,362 A | 1/1998 | Yoon |
| 5,707,390 A | 1/1998 | Bonutti |
| 5,711,299 A | 1/1998 | Manwaring et al. |
| 5,727,552 A | 3/1998 | Ryan |
| 5,735,795 A | 4/1998 | Young et al. |
| 5,748,767 A | 5/1998 | Raab |
| 5,754,623 A | 5/1998 | Seki |
| 5,757,881 A | 5/1998 | Hughes |
| 5,764,052 A | 6/1998 | Renger |
| 5,769,861 A | 6/1998 | Vilsmeier |
| 5,810,851 A | 9/1998 | Yoon |
| 5,840,148 A | 11/1998 | Campbell et al. |
| 5,868,673 A | 2/1999 | Vesely |
| 5,879,297 A | 3/1999 | Haynor et al. |
| 5,910,144 A | 6/1999 | Hayashi |
| 5,928,137 A | 7/1999 | Green |
| 5,951,481 A | 9/1999 | Evans |
| 5,957,934 A | 9/1999 | Rapoport |
| 5,989,265 A | 11/1999 | Bouquet de la Joliniere et al. |
| 6,026,818 A | 2/2000 | Blair et al. |
| 6,059,734 A | 5/2000 | Yoon |
| 6,061,644 A | 5/2000 | Leis |
| 6,067,465 A | 5/2000 | Foo et al. |
| 6,076,008 A | 6/2000 | Bucholz |
| 6,081,238 A | 6/2000 | Alicot |
| 6,082,366 A | 7/2000 | Andra et al. |
| 6,144,875 A | 11/2000 | Schweikard et al. |
| 6,161,009 A | 12/2000 | Skurdal et al. |
| 6,198,963 B1 | 3/2001 | Haim et al. |
| 6,222,544 B1 | 4/2001 | Tarr et al. |
| 6,246,900 B1 | 6/2001 | Cosman et al. |
| 6,307,473 B1 | 10/2001 | Zampini et al. |
| 6,325,758 B1 | 12/2001 | Carol et al. |
| 6,353,758 B1 | 3/2002 | Gliner et al. |
| 6,359,959 B1 | 3/2002 | Butler et al. |
| 6,360,116 B1 | 3/2002 | Jackson, Jr. et al. |
| 6,363,940 B1 | 4/2002 | Krag |
| 6,371,379 B1 | 4/2002 | Dames et al. |
| 6,377,162 B1 | 4/2002 | Delestienne et al. |
| 6,381,485 B1 | 4/2002 | Hunter et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,416,520 B1 | 7/2002 | Kynast et al. |
| 6,501,981 B1 | 12/2002 | Schweikard et al. |
| 6,510,199 B1 | 1/2003 | Hughes et al. |
| 6,526,415 B2 | 2/2003 | Smith et al. |
| 6,535,756 B1 | 3/2003 | Simon et al. |
| 6,650,930 B2 | 11/2003 | Ding |
| 6,662,036 B2 | 12/2003 | Cosman |
| 6,675,810 B2 | 1/2004 | Krag |
| 6,698,433 B2 | 3/2004 | Krag |
| 6,711,431 B2 | 3/2004 | Sarin et al. |
| 6,812,842 B2 | 11/2004 | Dimmer |
| 6,822,570 B2 | 11/2004 | Dimmer et al. |
| 6,838,990 B2 | 1/2005 | Dimmer |
| 6,882,947 B2 | 4/2005 | Levin |
| 6,889,833 B2 | 5/2005 | Seiler et al. |
| 6,918,919 B2 | 7/2005 | Krag |
| 6,934,356 B1 | 8/2005 | Satheesan et al. |
| 6,937,696 B1 | 8/2005 | Mostafavi |
| 6,977,504 B2 | 12/2005 | Wright et al. |
| 6,993,112 B2 | 1/2006 | Hesse |
| 6,999,555 B2 | 2/2006 | Morf |
| 7,026,927 B2 | 4/2006 | Wright et al. |
| 7,027,707 B2 | 4/2006 | Imaki |
| 7,072,707 B2 | 7/2006 | Galloway, Jr. et al. |
| 7,135,978 B2 | 11/2006 | Gisselberg et al. |
| 7,142,905 B2 | 11/2006 | Slayton et al. |
| 7,154,991 B2 | 12/2006 | Earnst et al. |
| 7,174,201 B2 | 2/2007 | Govari et al. |
| 7,176,798 B2 | 2/2007 | Dimmer et al. |
| 7,206,626 B2 | 4/2007 | Quaid, III |
| 7,206,627 B2 | 4/2007 | Abovitz et al. |
| 7,213,009 B2 | 5/2007 | Pestotnik et al. |
| 7,221,733 B1 | 5/2007 | Takai et al. |
| 7,280,863 B2 | 10/2007 | Shachar |
| 7,289,599 B2 | 10/2007 | Seppi et al. |
| 7,289,839 B2 | 10/2007 | Dimmer et al. |
| 7,318,805 B2 | 1/2008 | Schweikard et al. |
| 7,447,643 B1 | 11/2008 | Olson et al. |
| 7,557,353 B2 | 7/2009 | Black et al. |
| 7,587,234 B2 | 9/2009 | Owens et al. |
| 7,606,405 B2 | 10/2009 | Sawyer et al. |
| 7,657,301 B2 | 2/2010 | Mate et al. |
| 7,657,302 B2 | 2/2010 | Mate et al. |
| 7,657,303 B2 | 2/2010 | Mate et al. |
| 7,684,849 B2 | 3/2010 | Wright et al. |
| 7,912,529 B2 | 3/2011 | Herron et al. |
| 8,239,002 B2 | 8/2012 | Neustadter et al. |
| 8,239,005 B2 | 8/2012 | Wright et al. |
| 2001/0029509 A1 | 10/2001 | Smith et al. |
| 2002/0049362 A1 | 4/2002 | Ding |
| 2002/0065461 A1 | 5/2002 | Cosman |
| 2002/0083951 A1 | 7/2002 | Stegmaier et al. |
| 2002/0165443 A1 | 11/2002 | Mori |
| 2002/0188194 A1 | 12/2002 | Cosman |
| 2002/0193685 A1 | 12/2002 | Mate et al. |
| 2002/0193686 A1 | 12/2002 | Gilboa |
| 2003/0002621 A1 | 1/2003 | Hughes et al. |
| 2003/0023161 A1 | 1/2003 | Govari et al. |
| 2003/0052785 A1 | 3/2003 | Gisselberg et al. |
| 2003/0088178 A1 | 5/2003 | Owens et al. |
| 2003/0125616 A1 | 7/2003 | Black et al. |
| 2003/0153829 A1 | 8/2003 | Sarin et al. |
| 2003/0192557 A1 | 10/2003 | Krag et al. |
| 2003/0206610 A1 | 11/2003 | Collins |
| 2003/0206614 A1 | 11/2003 | Kendrick et al. |
| 2004/0019274 A1 | 1/2004 | Galloway et al. |
| 2004/0068182 A1 | 4/2004 | Misra |
| 2004/0096033 A1 | 5/2004 | Seppi et al. |
| 2004/0116804 A1 | 6/2004 | Mostafavi |
| 2004/0122308 A1 | 6/2004 | Ding |
| 2004/0122311 A1 | 6/2004 | Cosman |
| 2004/0122608 A1 | 6/2004 | Levin |

(56) References Cited

U.S. PATENT DOCUMENTS

| | | |
|---|---|---|
| 2004/0124105 A1 | 7/2004 | Seiler et al. |
| 2004/0125916 A1 | 7/2004 | Herron et al. |
| 2004/0127787 A1 | 7/2004 | Dimmer et al. |
| 2004/0133101 A1 | 7/2004 | Mate et al. |
| 2004/0138555 A1 | 7/2004 | Krag et al. |
| 2004/0158146 A1 | 8/2004 | Mate et al. |
| 2004/0176931 A1 | 9/2004 | Wright et al. |
| 2005/0059884 A1 | 3/2005 | Krag |
| 2005/0059887 A1 | 3/2005 | Mostafavi et al. |
| 2005/0077459 A1 | 4/2005 | Engler et al. |
| 2005/0085710 A1 | 4/2005 | Earnst et al. |
| 2005/0113855 A1 | 5/2005 | Kennedy et al. |
| 2005/0151649 A1 | 7/2005 | Wright et al. |
| 2005/0152495 A1 | 7/2005 | Hesse |
| 2005/0154280 A1 | 7/2005 | Wright et al. |
| 2005/0154283 A1 | 7/2005 | Wright et al. |
| 2005/0154284 A1 | 7/2005 | Wright et al. |
| 2005/0154293 A1 | 7/2005 | Gisselberg et al. |
| 2005/0195084 A1 | 9/2005 | Dimmer et al. |
| 2005/0203431 A1 | 9/2005 | Brodnick et al. |
| 2005/0234332 A1 | 10/2005 | Murphy |
| 2005/0261570 A1 | 11/2005 | Mate et al. |
| 2006/0052694 A1 | 3/2006 | Phillips et al. |
| 2006/0058648 A1 | 3/2006 | Meier et al. |
| 2006/0063999 A1 | 3/2006 | Herron et al. |
| 2006/0074301 A1 | 4/2006 | Meier et al. |
| 2006/0074302 A1 | 4/2006 | Meier et al. |
| 2006/0078086 A1 | 4/2006 | Riley et al. |
| 2006/0079764 A1 | 4/2006 | Wright et al. |
| 2006/0093089 A1 | 5/2006 | Vertatschitsch et al. |
| 2006/0100509 A1 | 5/2006 | Wright et al. |
| 2007/0161884 A1 | 7/2007 | Black et al. |
| 2008/0226149 A1 | 9/2008 | Wischmann et al. |

FOREIGN PATENT DOCUMENTS

| | | |
|---|---|---|
| JP | 2001-008947 | 1/2001 |
| WO | WO9525475 | 9/1995 |
| WO | WO9608208 | 3/1996 |
| WO | WO9712553 | 4/1997 |
| WO | WO9830166 | 7/1998 |
| WO | WO9838908 | 9/1998 |
| WO | WO9840026 | 9/1998 |
| WO | WO9927839 | 6/1999 |
| WO | WO9930182 | 6/1999 |
| WO | WO9933406 | 7/1999 |
| WO | WO9940869 | 8/1999 |
| WO | WO9958044 | 11/1999 |
| WO | WO9958065 | 11/1999 |
| WO | WO0038579 | 7/2000 |
| WO | WO0051514 | 9/2000 |
| WO | WO0053115 | 9/2000 |
| WO | WO0065989 | 11/2000 |
| WO | WO0239917 | 5/2002 |
| WO | WO0239918 | 5/2002 |
| WO | WO03053270 | 7/2003 |

OTHER PUBLICATIONS

Seppenwoolde et al, Precise and real-time measurement of 3D tumor motion in lung due to breathing and heartbeat, measured during radiotherapy, Int. J. Radiat. Oncol. Biol. Phys. Jul. 15, 2002, 53, pp. 822-834.

Sharp et al., Prediction of Respiratory Tumour Motion for Real-Time Image-Guided Radiotherapy, IPO Publishing Oltd.; Jan. 16, 2004, pp. 425-440.

Beyer, Thomas et al. "Dual-modality PET/CT Imaging: the effect of respiratory motion on combined image quality in clinical oncology." European journal of nuclear medicine and molecular imaging 30.4 (2003): 588-596.

Low, Daniel A., et al. "A method for the reconstruction of four-dimensional synchronized CT scans acquired during free breathing." Medical physics 30.6 (2003) 1254-1263.

Wolthaus, J. W. H., et al. "Fusion of respiration-correlated PET and CT scans: correlated lung tumour motion in anatomical and functional scans." Physics in medicine and biology 50.7 (2005): 1569.

positioning data structure — 300 patent identifier: 111-22-3333 — 301
session date: 7/15/2004 — 302
session start time: 4:11:05 pm — 303

| time | patient isocenter displacement | | | target tissue orientation | | individual transponder displacement | | | | | |
|---|---|---|---|---|---|---|---|---|---|---|---|
| | | | | | | #1 to #2 | | | #1 to #3 | | |
| | x | y | z | Θ | Φ | x | y | z | x | y | z |
| 4:11:05.002 PM | 0.0010 | -0.0009 | 0.0002 | 2.000 | -0.013 | -2.1031 | -1.3421 | -2.8102 | -1.2131 | 0.8231 | 3.6201 |
| 4:11:05.012 PM | 0.0021 | -0.0009 | -0.0001 | 1.543 | 0.034 | -2.0130 | -1.3421 | -2.8953 | -1.2213 | 0.8132 | 3.6205 |
| 4:11:05.022 PM | 0.9012 | -0.5986 | 0.0034 | 0.981 | 0.054 | -1.9032 | -1.3421 | -2.9302 | -1.4131 | 0.8021 | 3.6311 |
| 4:11:05.032 PM | 3.4213 | -1.2034 | 0.0681 | 0.087 | 0.072 | -1.8231 | -1.3421 | -2.8823 | -1.3820 | 0.7926 | 3.6503 |
| 4:11:05.042 PM | 2.8312 | -1.1044 | 0.0612 | 0.154 | 0.030 | -2.2071 | -1.3421 | -2.8732 | -1.2180 | 0.8031 | 3.6412 |
| 4:11:05.052 PM | 0.012 | -0.0011 | 0.0007 | 1.832 | -0.023 | -2.1096 | -1.3421 | -2.8104 | -1.2155 | 0.8244 | 3.6164 |

*FIG. 3*

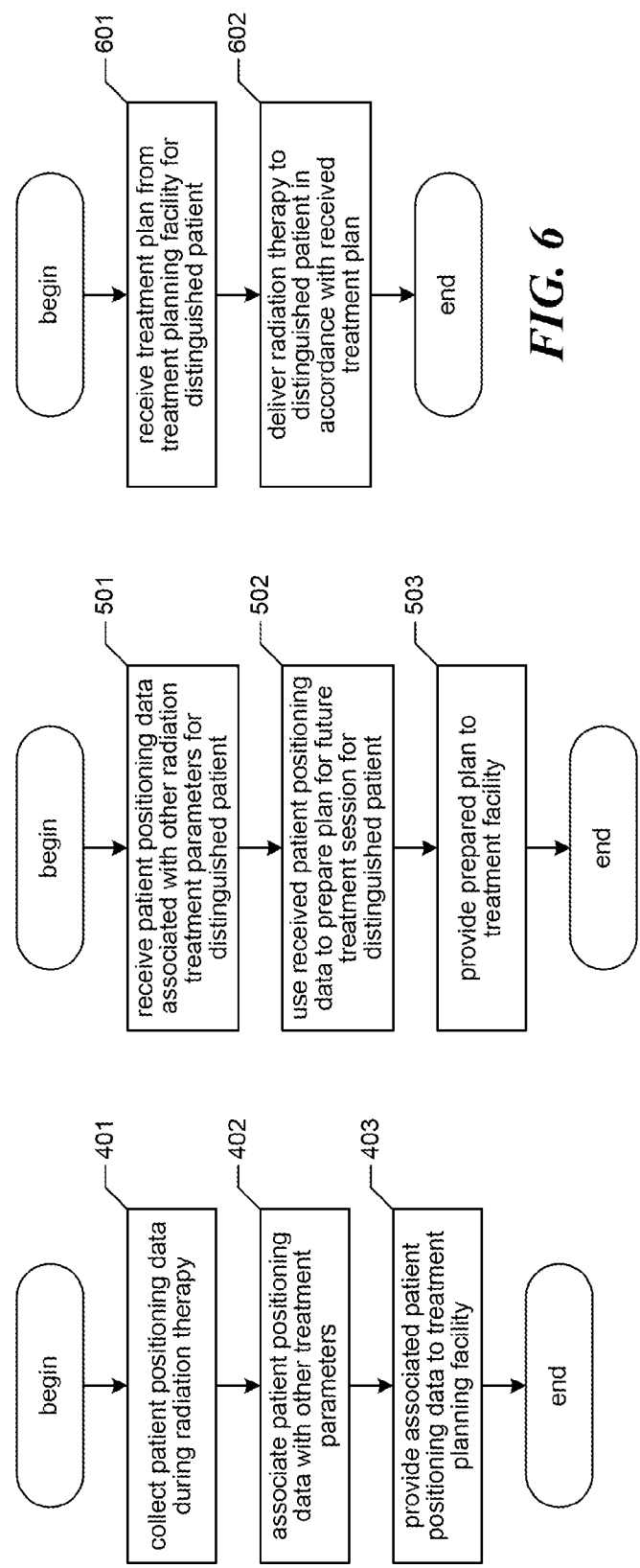

| field | gantry position | collimator settings | intensity level | session planning ⎯700 duration ⎯701 ⎯702 |
|---|---|---|---|---|
| field 1 | gantry position 1 | collimator settings 1 | intensity level 1 | duration 1 |
| field 2 | gantry position 2 | collimator settings 2 | intensity level 2 | duration 2 |
| 711 | 712 | 713 | 714 | 715 |

FIG. 7

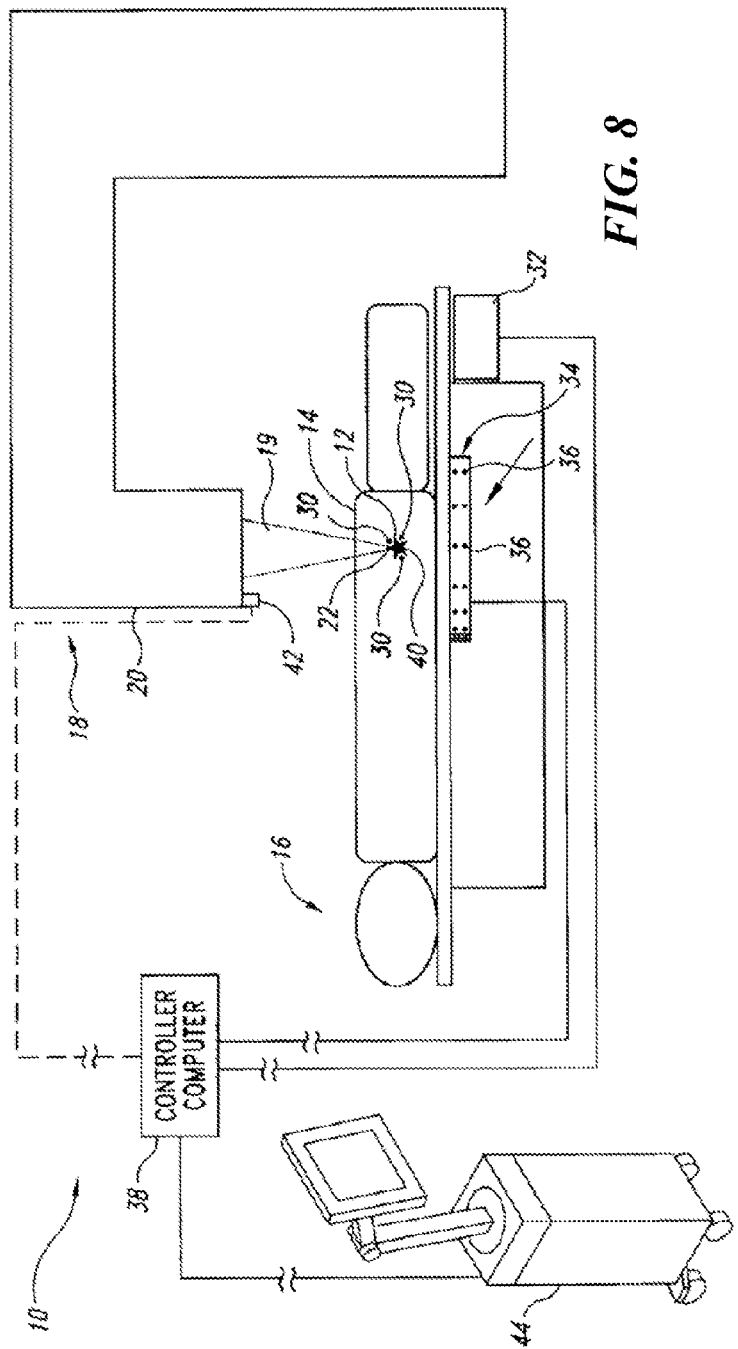
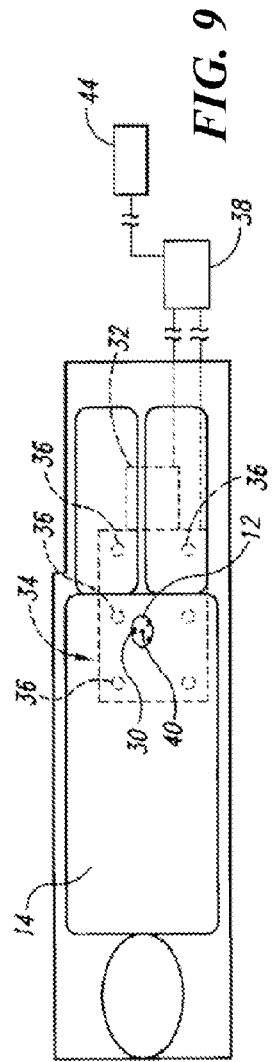

DYNAMIC/ADAPTIVE TREATMENT PLANNING FOR RADIATION THERAPY

CROSS-REFERENCE TO RELATED APPLICATIONS

This application is a continuation of U.S. patent application Ser. No. 11/189,431 filed Jul. 25, 2005, which claims the benefit of U.S. Patent Application No. 60/590,503 filed Jul. 23, 2004, which is hereby incorporated by reference in its entirety.

TECHNICAL FIELD

The present invention is directed to the field of software for planning radiation therapy.

BACKGROUND

Radiation therapy can be used to treat localized cancer. In a typical application, a radiation delivery system has an ionizing radiation device mounted to a movable gantry. The radiation delivery system controls the motion of the radiation device to direct an ionizing radiation beam to a specific point in space commonly referred to as the "machine isocenter." During radiation therapy, a patient is positioned so that the patient's tumor is located at the machine isocenter throughout treatment.

Radiation is typically delivered to a patient during a radiation therapy session in accordance with a session plan. A session plan typically specifies, for each of one or more "treatment fields," such information as the gantry position, which determines the path that radiation energy will take to the tumor during the treatment field; collimator settings that determine the shape and cross-sectional area of the radiation energy beam; the intensity level of the radiation beam; and a duration that determines for how much time radiation energy will be delivered during the field. Various session plans may include different or additional information, however.

A plan is typically prepared using determinants such as the following: the tumor's mass, volume, shape, orientation, location in the body, and proximity to different organs and other anatomical structures; and information about radiation energy intended to be delivered to the tumor in foregoing radiation therapy sessions, as well as other approaches previously used to treat the tumor. Various plan preparation techniques may use fewer, more, or different determinants, however.

Conventionally, a batch of several session plans are prepared for a number of future sessions in advance of the sessions. In this batch approach to session plan preparation, the individual plans of the batch are often homogeneous, and assume either (1) no relevant changes in the patient's condition during the course of the batch, or (2) projected changes in the patient's condition determined in advance. This approach further typically assumes (1) that radiation has been and will be delivered in accordance with each plan with complete accuracy, or (2) that radiation has been and will be delivered in accordance with each plan at a projected level of accuracy determined in advance.

The batch approach to session plan preparation has the disadvantage that each plan of a batch after the first plan is based upon important assumptions that may in many cases be unwarranted. As a result, individual plans prepared using the batch approach may have various deficiencies, which have the effect of degrading the effectiveness of radiation therapy in treating the tumor.

In view the foregoing, and approach to session plan preparation having a reduced reliance on such important assumptions would have significant utility.

BRIEF DESCRIPTION OF THE DRAWINGS

FIG. 3 is a data structure diagram showing typical contents of a positioning data structure provided by a tracking system for use in adaptive treatment planning.

FIG. 4 is a flow diagram showing steps typically performed by the facility in order to prepare positioning data for use in preparing adaptive treatment plans.

FIG. 5 is a flow diagram showing steps typically performed by the facility to generate an adaptive treatment plan using patient positioning data.

FIG. 6 is a flow diagram showing steps typically performed by the facility in order to conduct a radiation treatment session in accordance with an adaptive treatment plan.

FIG. 7 is a table diagram showing a session plan typical of those used to conduct treatment sessions for which the facility provides tracking information, and/or those produced using tracking information provided by the facility.

FIG. 8 and FIG. 9 illustrate a system and several components for locating, tracking and monitoring a target within a body.

DETAILED DESCRIPTION

A software facility for facilitating and/or performing dynamic and/or adaptive treatment planning for radiation therapy ("the facility") is described. The facility provides or uses the output of a patient tracking system for one or more past radiation therapy sessions for a patient to plan one or more future sessions for the patient. In particular, embodiments of the facility provide or use information about the position and/or orientation of a patient isocenter relative to the machine isocenter throughout some or all of the time that radiation energy was delivered during the past sessions, in a manner that can be correlated or otherwise associated with information about the planned and/or actual delivery of radiation during the past sessions. As one example, embodiments of the facility provide or use information about patient position and/or orientation in time-series form, enabling this information to be correlated with planned and/or actual delivery of radiation also in time-series form.

In some embodiments, the facility provides patient position and/or orientation information to—or in a form usable by—an external treatment planning mechanism. In some embodiments, the facility directly performs treatment planning using patient position and/or orientation information. In some embodiments, the facility delivers radiation energy in a later treatment session based upon patient position and/or orientation during one or more past treatment sessions.

In addition to the position and/or orientation of the patient isocenter relative to the machine isocenter, information from past treatment sessions provided for use in future treatment planning can include the relative position and/or relative orientation of implanted fiducials or other markers, such as the passive magnetic transponders described in U.S. Pat. No. 7,912,529, entitled PANEL-TYPE SENSOR/SOURCE ARRAY ASSEMBLY, filed Dec. 30, 2002; U.S. patent application Ser. No. 09/877,498, entitled GUIDED RADIATION THERAPY SYSTEM, filed Jun. 8, 2001; U.S. Pat. No. 7,747,307, entitled METHOD AND SYSTEM FOR MARKER LOCALIZATION, filed Oct. 6, 2003; U.S. Pat. No. 8,196,589, entitled IMPLANTABLE MARKER WITH WIRELESS SIGNAL TRANSMITTAL, filed Dec. 24, 2003; and U.S. patent application Ser. No. 10/749,478, entitled RECEIVER USED IN MARKER LOCALIZATION SENSING SYSTEM, filed Dec. 31, 2003, each of which is hereby incorporated by reference in its entirety.

By providing or using patient tracking information from one or more past radiation therapy sessions to plan one or more future radiation therapy sessions in some or all of the ways described above, the facility can reduce the reliance on assumptions required for session planning, potentially improving the effectiveness of treatment in accordance with the resulting treatment plans.

Figure 1:
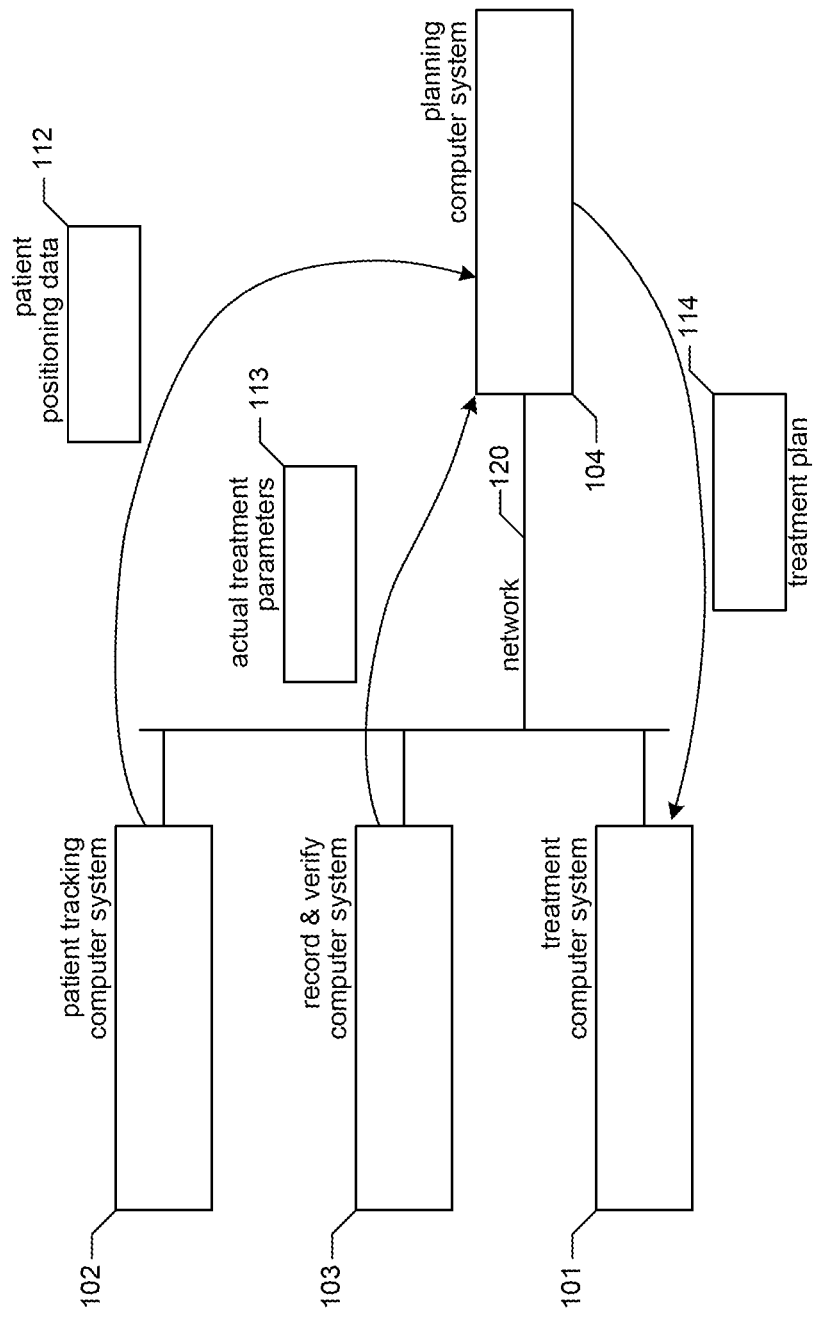
FIG. 1 is a network diagram showing an example of a set of connected computer systems used by the facility.

FIG. 1 is a network diagram showing an example of a set of connected computer systems used by the facility. These include a treatment computer system 101 that controls the delivery of radiation therapy; a patient tracking computer system 102 that, while radiation therapy is being delivered under the control of the treatment computer system, tracks the position of the patient and generates patient positioning data 112, discussed below in conjunction with FIG. 3; a record and verify computer system 103 that, while radiation therapy is being delivered under the control of the treatment computer system, records the actual treatment parameters 113, such as gantry position, beam on/off, beam intensity, beam shape (i.e., collimator settings), etc.; and a planning computer system 104 that receives patient positioning data and actual treatment parameters and uses them to generate one or more treatment plans 114 for the same patient, which it provides to the treatment computer system.

In some embodiments, the facility uses the patient tracking computer system to obtain patient positioning data during a period of time when the patient is not undergoing radiation therapy. As one example, the patient tracking computer system may collect patient positioning data during a patient observation phase preceding radiation therapy treatment, during which the present position of the target location within the patient's body and/or its pattern of movement within the patient's body is determined in preparation for radiation therapy. In various embodiments, this phase can be performed inside or outside the treatment vault. As another example, the patient tracking computer system may collect patient positioning data during a treatment rehearsal phase inside the treatment vault. Such a rehearsal phase may be performed, for example, to ensure that all of the physical activity anticipated during the actual treatment session, such as movement of the linear accelerator and/or other equipment resident in the vault, can be successfully performed in the presence of the patient. In these embodiments, it is typical for the facility to transmit the collected patient positioning data to the planning computer system without accompanying actual treatment parameters, and for the planning computer system to create or adapt a treatment plan based on this unaccompanied patient positioning data.

In some cases, computer systems 101-103 are connected by one or more data networks 120. In some embodiments, some or all of data 112-114 are transferred between computer systems in a way other than using a network, such as by storing this data on removable media physically transferred between the computer systems.

In some embodiments, the facility uses a different set of computer systems, including sets including additional computer systems, sets including fewer computer systems, or sets in which the functionality of different computer systems is divided or consolidated. As examples, the patient tracking computer system can be consolidated with the treatment computer system, the planning computer system may be consolidated with the patient tracking computer system, the planning computer system may be consolidated with the treatment computer system, all three computer systems may be consolidated together, etc.

In some embodiments, the facility uses or operates in conjunction with hardware and/or software as described U.S. patent application No. 60/590,697, entitled USER INTERFACE FOR GUIDED RADIATION THERAPY, filed Jul. 23, 2004, and U.S. Pat. No. 7,899,513, entitled MODULAR SOFTWARE SYSTEM FOR GUIDED RADIATION THERAPY, filed Jul. 25, 2005, each of which is hereby incorporated by reference in its entirety.

Figure 2:
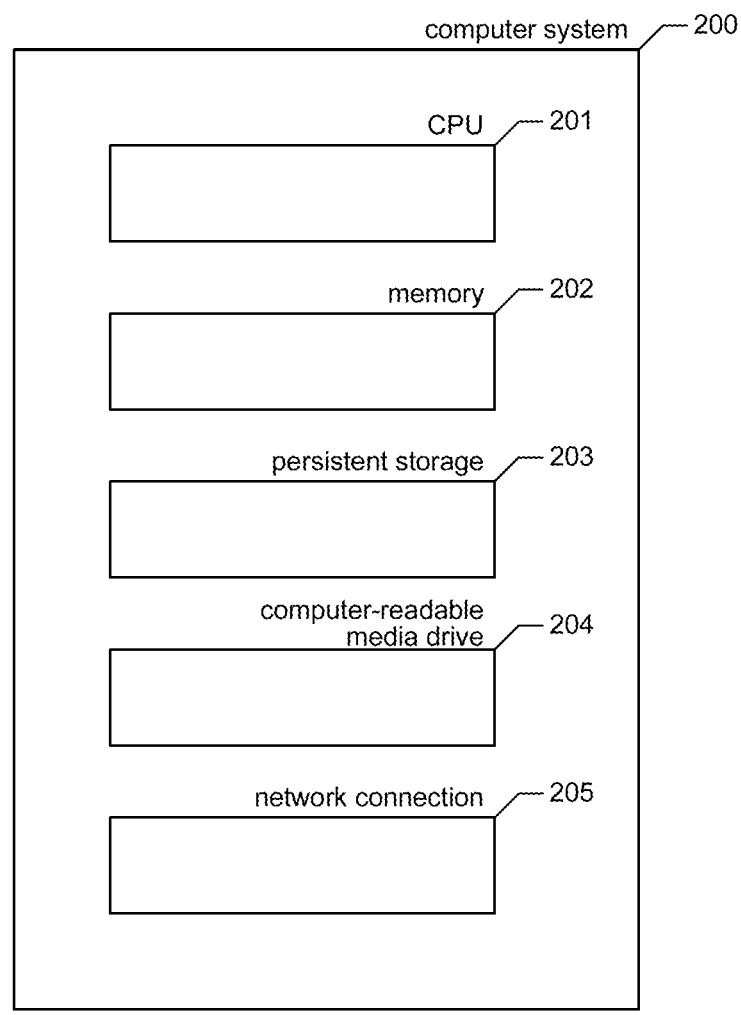
FIG. 2 is a block diagram showing some of the components typically incorporated in at least some of the computer systems and other devices on which the facility executes.

FIG. 2 is a block diagram showing some of the components typically incorporated in at least some of the computer systems and other devices on which the facility executes. These computer systems and devices 200 may include one or more central processing units ("CPUs") 201 for executing computer programs; a computer memory 202 for storing programs and data—including data structures—while they are being used; a persistent storage device 203, such as a hard drive, for persistently storing programs and data; a computer-readable media drive 204, such as a CD-ROM drive, for reading programs and data stored on a computer-readable medium; and a network connection 205 for connecting the computer system to other computer systems, such as via the Internet, to exchange programs and/or data—including data structures. While computer systems configured as described above are typically used to support the operation of the facility, one of ordinary skill in the art will appreciate that the facility may be implemented using devices of various types and configurations, and having various components.

FIG. 3 is a data structure diagram showing typical contents of a positioning data structure provided by a tracking system for use in adaptive treatment planning. The positioning data structure 300 includes information identifying the patient and session to which the positioning data it includes relates, including patient identifying information 301, such as a social security number; the date 302 on which the session was performed; and the time 303 at which the session began. The data structure further includes substantive positioning information, shown in table 310. Table 310 is made up of rows, such as rows 311-316, each corresponding to a different time during the treatment session. In some embodiments, the times to which the rows correspond occur at regular or semi-regular intervals—here, at intervals of 0.010 seconds. Each row contains an indication of the time as well as positioning data occurring at that time, organized into the following columns: a time column 321 containing the time; a group of patient isocenter displacement columns 322-324, one for each of three rectangular dimensions; a group of target tissue orientation columns 325-326 each containing one of two angular orientation coordinates for target tissue surrounding the patient isocenter; and groups of individual transponder displacement columns, such as columns 327-329 and 330-332, each containing a displacement component in a particular dimension between a pair of transponders. For example, row 311 indicates that, at time 4:11:05.002 PM, the patient isocenter was +0.0010 centimeters from the machine isocenter in the x dimension, −0.0009 centimeters from the machine isocenter in the y dimension, and +0.0002 centimeters from the machine isocenter in the z dimension. The row further indicates that the target tissue is +2.000 degrees from a reference axis associated with the machine isocenter in the theta dimension, and −0.013 degrees from the reference axis in the phi dimension. Row 311 further indicates that the displacement from transponder #1 to transponder #2 in the x dimension is −2.1031, in the y dimension is −1.3421, and in the z dimension it is −2.8102. Row 311 further indicates that the displacement from transponder #1 to transponder #3 in the x dimension is −1.2131, in the y dimension is +0.8231, and in the z dimension is +3.6201.

The facility may adapt treatment plans for a patient based upon deviations in the positioning information contained in the positioning data structure. For example, rows 313-315 reflect a fairly significant deviation in patient isocenter displacement in the x and y dimensions. The facility may, for example, increase an integrated dose associated with a future treatment plan based upon the likelihood that this deviation caused the actual integrated dose in the Jul. 15, 2004 session to fall short of the planned integrated dose for that session. The facility may similarly respond to deviations in other patient positioning information, such as target tissue orientation, transponder displacement, transponder orientation, etc.

Those skilled in the art will appreciate that the facility may use positioning data structures having various contents and formats. For example, the facility may use positioning data structures that contain more, less, or different patient and session identifying information, and/or positioning data structures that contain more, less, or different substantive positioning information, or substantive positioning information in different units, coordinate schemes, etc. The positioning data structure may be expressed in a variety of formats, such as the format shown one of a number of existing or new tag-based markup languages, such as XML or a variant; or a compliant or non-compliant version of a standard format for transferring digital medical images or other digital medical data, such as present or future versions of the Digital Imaging and Communications in Medicine, or "DICOM," format adopted by the National Electrical Manufacturers Association, described at xray.hmc.psu.edu/physresources/dicom/index.html. The positioning data structure may be organized in a variety of ways, and may be compressed and/or encrypted in a variety of ways. One sample alternative data structure organization is shown in U.S. Patent Application No. 60/590,693, entitled DATA PROCESSING FOR REAL-TIME TRACKING OF A TARGET IN RADIATION THERAPY, filed Jul. 23, 2004, and U.S. Pat. No. 8,095,203, entitled DATA PROCESSING FOR REAL-TIME TRACKING OF A TARGET IN RADIATION THERAPY, filed concurrently herewith, each of which is hereby incorporated by reference in its entirety.

FIGS. 4-6 are flow diagrams showing sets of steps typically performed by the facility.

FIG. 4 is a flow diagram showing steps typically performed by the facility in order to prepare positioning data for use in preparing adaptive treatment plans. In step 401, the facility collects patient positioning data for a patient during a radiation therapy session. The data collection of step 401 is described in greater detail in U.S. patent application Ser. No. 11/166,801, entitled SYSTEMS AND METHODS FOR REAL TIME TRACKING OF TARGETS IN RADIATION THERAPY AND OTHER MEDICAL APPLICATIONS, filed Jun. 24, 2005; U.S. Patent Application No. 60/590,693, entitled DATA PROCESSING FOR REAL-TIME TRACKING OF A TARGET IN RADIATION THERAPY, filed Jul. 23, 2004, and U.S. Pat. No. 8,095,693, entitled DATA PROCESSING FOR REAL-TIME TRACKING OF A TARGET IN RADIATION THERAPY, filed Jul. 25, 2005, each of which is hereby incorporated by reference in its entirety.

In step 402, the facility associates the patient positioning data collected in step 401 with other treatment parameters. Such association may reflect a time-based correlation, or associations of other types. The patient positioning data can be associated with a wide variety of treatment parameters, including beam activation, beam intensity, collimator settings, gantry positions, etc. Patient positioning data may be associated with planned treatment parameters, actual treatment parameters, or a combination thereof. In step 403, the facility provides the patient positioning data associated in step 402 to a treatment planning facility. After step 403, these steps conclude.

FIG. 5 is a flow diagram showing steps typically performed by the facility to generate an adaptive treatment plan using patient positioning data. In step 501, the facility receives patient positioning data associated with other radiation treatment parameters for a distinguished patient. Such patient positioning data can correspond to one or more past treatment sessions for the distinguished patient. In step 502, the facility uses the received patient positioning data to prepare a plan for a future treatment session for the distinguished patient. In some embodiments, in step 502, the facility uses the received patient positioning data in connection with the radiation treatment parameters with which it is associated. In some embodiments, the plan prepared by the facility specifies, for each of one or more treatment fractions, treatment parameters such as fraction duration, radiation energy delivery rate, radiation energy delivery direction, radiation energy beam shape, radiation beam cross-sectional area, etc. In some embodiments, the facility prepares the plan in a manner that compensates for deviations between the "integrated" radiation dose planned to be accumulated at a point, in a volume, in each of an array of subvolumes, etc., over the course of the past session, and the integrated dose actually delivered, such as by inversely varying the corresponding integrated radiation dose provided in the plan for the next session. In some embodiments, the facility prepares the plan in a manner that adjusts to and/or compensates for short- or long-term migration or rotation of the tumor, deformation of the tumor, contraction or expansion of the tumor, or other qualitative changes to the tumor observable via changes in the relative or absolute positions of transponders or other available data. In step 503, the facility provides the prepared plan to a treatment facility. After step 503, these steps conclude.

FIG. 6 is a flow diagram showing steps typically performed by the facility in order to conduct a radiation treatment session in accordance with an adaptive treatment plan. In step 601, the facility receives the adaptive treatment plan from a treatment planning facility for a distinguished patient. In step 602, the facility delivers radiation therapy to the distinguished patient in accordance with the received treatment plan. After step 602, these steps conclude.

FIG. 7 is a table diagram showing a session plan typical of those used to conduct treatment session for which the facility provides tracking information, and/or those produced using tracking information provided by the facility. The session plan 700 is made up of rows, such as rows 701 and 702, each corresponding to a different treatment field. Each row is divided into the following columns: a treatment field column 711 containing information identifying the treatment field; a gantry position column 712 which determines the path that radiation energy will take to the tumor during the treatment field; a collimator settings column 713 that determine the shape and cross sectional area of the radiation energy beam; an intensity level column 714 that specifies the intensity level of the radiation beam; and a duration column 715 that determines for how much time radiation energy will be delivered during the field.

FIGS. 8-23 illustrate a system and several components for locating, tracking and monitoring a target within a body in accordance with embodiments of the present invention. The system and components are usable to locate, track, monitor, and evaluate a target for application of a selected therapy to the target, such as guided radiation therapy. Several of the components described below with reference to FIGS. 8-23 can also be used in systems for performing methods in accordance with aspects of the present invention. Therefore, like reference numbers refer to like components and features throughout the various figures.

FIGS. 8, 9, 22, and 23 illustrate various aspects of a radiation therapy system for applying guided radiation therapy to a target 12 (e.g., a tumor) within a lung 4, prostate, breast, head, neck or other part of a patient 14. The radiation therapy system has a localization system 10 and a radiation delivery device 18. The localization system 10 is a tracking unit that locates and tracks the actual position of the target 12 in real time during treatment planning, patient setup, and/or while applying ionizing radiation to the target from the radiation delivery device. Thus, although the target 12 may move within the patient because of breathing, organ filling/emptying, cardiac functions or other internal movement as described above, the localization system 10 accurately tracks the motion of the target relative to the external reference frame of the radiation delivery device or other external reference frame outside of the patient to accurately deliver radiation within a small margin around the target. The localization system 10 can also monitor the configuration and trajectory of the marker to provide an early indicator of a change in the tumor without using ionizing radiation. Moreover, the localization system 10 continuously tracks the target and provides objective data (e.g., three-dimensional coordinates in an absolute reference frame) to a memory device, user interface, linear accelerator, and/or other device. The system is described below in the context of guided radiation therapy for treating a tumor or other target in the lung of the patient, but the system can be used for tracking and monitoring the prostate gland or other targets within the patient for other therapeutic and/or diagnostic purposes.

The tracking unit is responsible for generating patient tracking records each indicating the current location and/or orientation of a patient isocenter relative to a reference point, such as relative to a machine isocenter during radiation treatment.

In some embodiments, the tracking unit computes patient tracking records with no more than a maximum latency after the time of the underlying measurements, such as a maximum latency of 50 milliseconds, or a maximum latency of 200 milliseconds. In some embodiments, the tracking unit generates patient tracking records at least a minimum frequency, such as a minimum frequency of 20 hertz. Additional detail about the generation of patient tracking records is discussed in U.S. patent application Ser. No. 11/166,801, entitled SYSTEMS AND METHODS FOR REAL TIME TRACKING OF TARGETS IN RADIATION THERAPY AND OTHER MEDICAL APPLICATIONS, filed Jun. 24, 2005 and incorporated by reference in its entirety.

The radiation delivery source of the illustrated embodiment is an ionizing radiation device 18 (i.e., a linear accelerator). Suitable linear accelerators are manufactured by Varian Medical Systems, Inc. of Palo Alto, Calif.; Siemens Medical Systems, Inc. of Iselin, N.J.; Elekta Instruments, Inc. of Iselin, N.J.; or Mitsubishi Denki Kabushik Kaisha of Japan. Such linear accelerators can deliver conventional single or multi-field radiation therapy, 3D conformal radiation therapy (3D CRT), intensity modulated radiation therapy (IMRT), stereotactic radiotherapy, and tomo therapy. The radiation delivery source 20 can deliver a gated, contoured or shaped beam 19 of ionizing radiation from a movable gantry 20 to an area or volume at a known location in an external, absolute reference frame relative to the radiation delivery source 18. The point or volume to which the ionizing radiation beam 19 is directed is referred to as the machine isocenter.

The tracking system includes the localization system 10 and one or more markers 30. The localization system 10 determines the actual location of the markers 30 in a three-dimensional reference frame, and the markers 30 are typically implanted within the patient 16. In the embodiment illustrated in FIGS. 22 and 23, more specifically, three markers identified individually as markers 30a-c are implanted in or near the lung 4 of the patient 16 at locations in or near the target 12. In other applications, a single marker, two markers, or more than three markers can be used depending upon the particular application. Two markers, for example, are desirable because the location of the target can be determined accurately, and also because any relative displacement between the two markers over time can be used to monitor marker migration in the patient. The markers 30 are desirably placed relative to the target 12 such that the markers 30 are at least substantially fixed relative to the target 12 (e.g., the markers move directly with the target or at least in direct proportion to the movement of the target). The relative positions between the markers 30 and the relative positions between a target isocenter T of the target 12 and the markers 30 can be determined with respect to an external reference frame defined by a CT scanner or other type of imaging system during a treatment planning stage before the patient is placed on the table. In the particular embodiment of the system illustrated in FIGS. 22 and 23, the localization system 10 tracks the three-dimensional coordinates of the markers 30 in real time relative to an absolute external reference frame during the patient setup process and while irradiating the patient to mitigate collateral effects on adjacent healthy tissue and to ensure that the desired dosage is applied to the target.

The localization system 10 provides several features, either individually or in combination with each other, that enhance the ability to accurately deliver high doses of radiation to targets within tight margins. For example, many embodiments of the localization system use leadless markers that are implanted in the patient so that they are substantially fixed with respect to the target. The markers accordingly move either directly with the target or in a relationship proportional to the movement of the target. As a result, internal movement of the target caused by respiration, organ filling, cardiac functions, or other factors can be identified and accurately tracked before, during and after medical procedures. Moreover, many aspects of the localization system 10 use a non-ionizing energy to track the leadless markers in an external, absolute reference frame in a manner that provides objective output. In general, the objective output is determined in a computer system without having a human interpret data (e.g., images) while the localization system 10 tracks the target and provides the objective output. This significantly reduces the latency between the time when the position of the marker is sensed and the objective output is provided to a device or a user. For example, this enables an objective output responsive to the location of the target to be provided at least substantially contemporaneously with collecting the position data of the marker. The system also effectively eliminates inter-user variability associated with subjective interpretation of data (e.g., images).

The illustrated system 10 includes a plurality of markers 30 positioned in or adjacent to the target 12 to mark the target's actual location in the body 14. Accordingly, the markers 30 are markers in, on or near the body. In one example, the markers 30 may be attached to patient-immobilization devices at known locations relative to the treatment isocenter. The markers 30 are energized or excited by an excitation source 32 positioned exterior of the patient's body 14. When the markers 30 are excited, they each resonate at a selected unique frequency and generate a low energy radio-frequency magnetic signal measurable from outside of the body 14. The signals from the markers 30 are detected and measured by an array 34 of sensors 36 located exterior of the patient's body 14. The sensors 36 are positioned in a fixed, selected geometry relative to each other, so the array 34 defines a fixed reference coordinate system from which location and movement are calculated. The sensors 36 are operatively coupled to a computer controller 38 that receives the measurement information from each sensor and determines the actual location of the markers 30 within the patient's body 14 relative to the sensors.

In one embodiment, the computer controller 38 includes algorithms used to define and determine the location of the target isocenter 40 within the target 12, based upon the signal measurements by the sensors 36 from the resonating markers. In another embodiment, the location of the target isocenter 40 within the target 12 is selected, and the computer controller 38 utilizes position information about the position and/or orientation of each marker 30 relative to the selected target isocenter. The target isocenter 40 is the point or position within the target to which the shaped dose of radiation is configured around or referenced to as determined by a treatment planning process. In one embodiment, the sensors 36 are polled twelve or more times per minute to track the actual position of the target isocenter 40 within the patient's body 14 relative to the sensor array 34. Accordingly, the actual position of the target 12 and the target isocenter 40 can be monitored in real time when the patient is positioned adjacent to the sensor array 34.

The actual position of the target isocenter 40 is compared to the position of the machine isocenter 22 relative to the sensor array 34. The illustrated system 10 has a reference device 42 positioned on the gantry 20 of the linear actuator or another selected position on a radiation therapy delivery device used in alternate embodiments. In these alternate embodiments, the other radiation therapy delivery device can include cobalt machines, a Gamma Knife, a Cyberknife, specialized stereostatic radiotherapy devices, or a TomoCT assembly (which utilizes a linear actuator in a CT scanner). The reference device 42 is positioned at a known spatial or geometric relationship relative to the machine isocenter 22. The reference device 42 in one embodiment is a resonating, three axis, single frequency marker that provides a measurable signal detectable by the sensors 36 in the array 34. The reference device 42 in alternate embodiments can be positioned in a remote location away from the gantry 20. In either embodiment, the location of the machine isocenter 22 relative to the sensor array 34 can be calculated upon determining the position of the reference device 42 relative to the sensor array. The sensors 36 provide the measurement data about the reference device 42 to the computer controller 38, and the computer controller calculates the location of the machine isocenter 22 relative to the sensor array 34.

The location of the target isocenter 40 relative to the sensor array 34 is compared to the position of the machine isocenter 22 relative to the sensor array. If the target isocenter 40 and machine isocenter 22 are spatially misaligned such that the two isocenters are not three-dimensionally coincident with each other, the patient 16, and/or target 12 can be moved relative to the machine isocenter 22. The target 12 position is moved until the target isocenter 40 is coincident with the machine isocenter 22. Once the target and machine isocenters 40 and 22 are acceptably aligned, the radiation delivery source 18 can be activated to provide the ionizing radiation beam 19 referenced to the target isocenter, thereby irradiating the target according to a radiation treatment plan, while minimizing or eliminating collateral damage to healthy tissue surrounding the target 12. The actual location of the target isocenter 40 can also be monitored in real time during the radiation therapy to ensure that the target isocenter does not move an unacceptable amount relative to the machine isocenter 22 and allow for treatment when the treatment isocenter and the machine isocenter are within acceptable displacement limits.

In the illustrated embodiment, the system 10 also includes a monitoring assembly 44 coupled to the computer controller 38 that provides feedback data to a user interface for the doctor or technician operating the system and/or the radiation delivery device 18. As an example, the monitoring assembly 44 can provide the feedback data as a visual representation of the target isocenter's position in three-dimensional space relative to the machine isocenter's position in real time as the patient is being set up and positioned for the radiation therapy. The monitoring assembly 44 can also provide other feedback data to the user interface including, for example, confirmation of setup completion, graphical information, patient information, radiation treatment plan information, or other information that can be utilized during the guided radiation therapy process.

Figure 10:
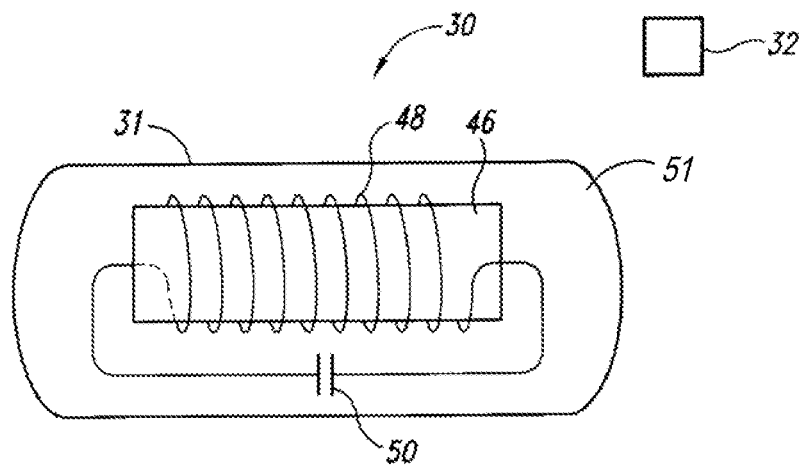
FIG. 10, FIG. 11, and FIG. 12 illustrate excitable markers.
Figure 11:
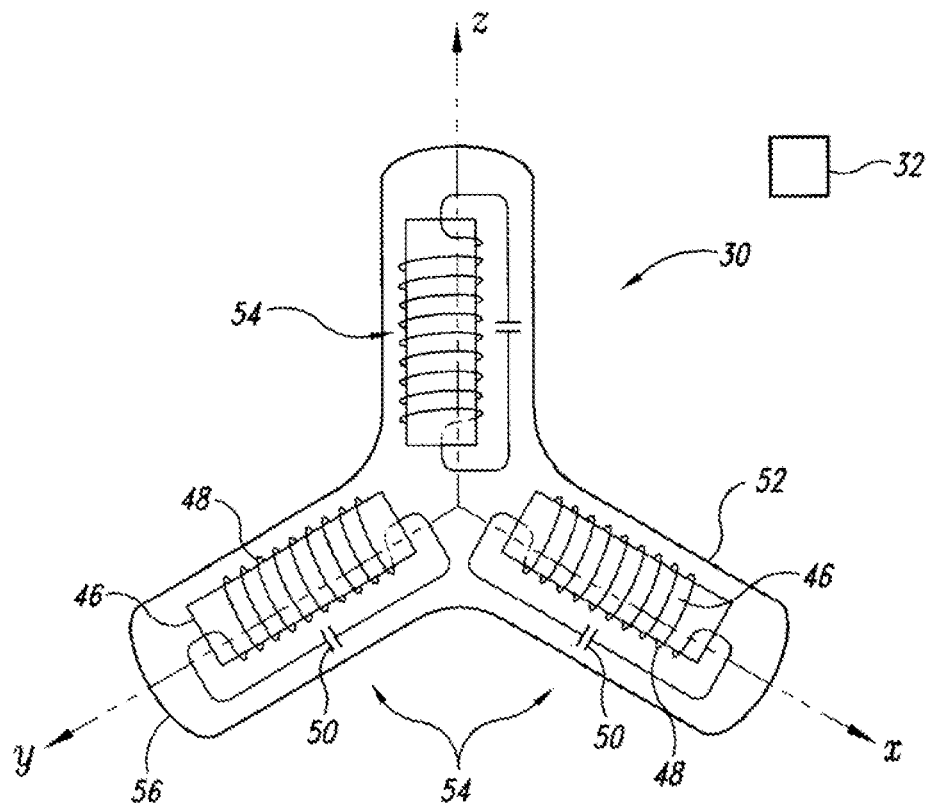
Figure 12:
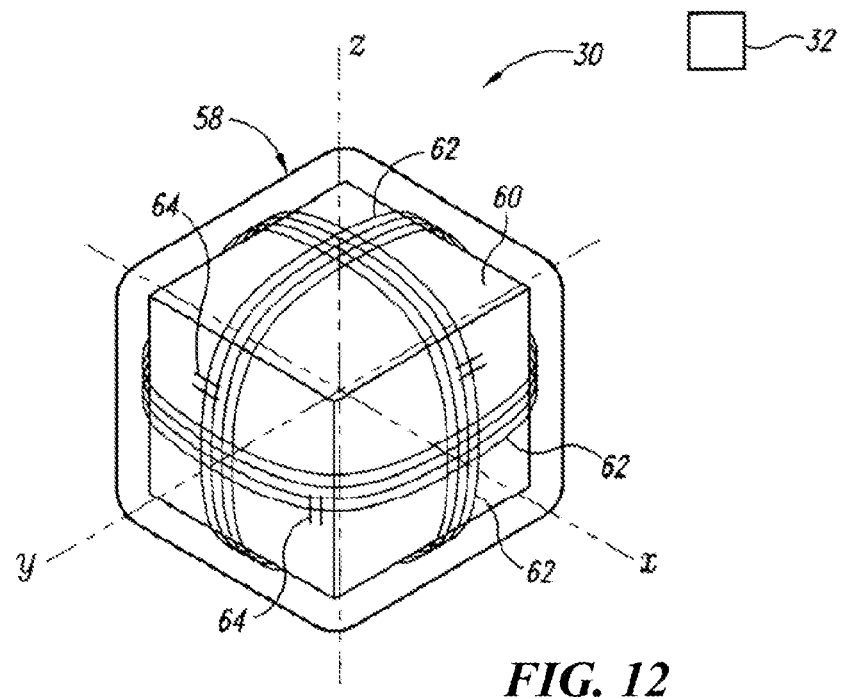

FIGS. 10-12 illustrate excitable markers 30 of alternate embodiments usable in the system 10. One of the markers 30 shown in FIG. 10 is an implantable, single-axis, resonating marker 31 having a ferrite core 46 wrapped by a conductive winding 48, and the winding is connected to a small capacitor 50. The marker 31 is configured to be energized by the external excitation source 32, which produces an electromagnetic field. This electromagnetic field causes the marker 31 to resonate at a predetermined frequency, thereby providing a signal of sufficient intensity to be measured by the sensors 36 (FIG. 8) from outside of the body. A biologically inert coating 52 encapsulates the ferrite core 46, the winding 48, and the capacitor 50 so as to provide a small, self-contained, wireless excitable marker 31 that can be permanently implanted into the patient. In this embodiment, the marker 31 is "wireless" because it need not be physically connected via wires to an outside energy source for generation or communication of the marker signal. In one embodiment, the marker 31 has a length of only approximately 5 mm and diameter sized to fit through an applicator needle. The marker 31 in other embodiments can have different sizes as needed for the desired configuration of the marker signal.

As best seen in FIG. 11, another one of the excitable markers 30 includes a three-axis, wireless, resonating marker 52 with three signaling portions 54. Each signaling portion 54 is positioned axially perpendicular to the other two signaling portions. Accordingly, the three signaling portions 54 define an X, Y, Z reference coordinate. Each of the signaling portions 54 includes a ferrite core 46, a winding 48 around the ferrite core, and a small capacitor 50 connected to each winding. Each signaling portion is configured to be energized by the external excitation source 32, and to resonate at a frequency different than the resonating frequency of the other two signaling portions.

In one embodiment, as illustrated in FIG. 11, the three-axis marker 52 includes a biologically inert coating 56 that encapsulates all three of the signaling portions 54, so the marker can be permanently implanted in the patient's body. When the marker 52 is energized by the external excitation source 32, each of the marker's signaling portions resonates at its selected frequency and provides the measurable marker signal at an intensity so it can each be measured by the sensor array 34 (FIG. 8). Frequency multiplexing by the computer controller allows the computer controller 38 to differentiate between the marker signals from the different signaling portions of the marker when calculating the marker's position and orientation relative to the sensor array.

As best seen in FIG. 12, another embodiment of the marker 30 includes a cube-shaped marker 58 with a single ferrite core 60 and three sets of windings 62 axially oriented perpendicular to each other to define the X, Y, and Z axes for the marker. Each winding 62 is connected to a small capacitor 64 and configured to resonate at a frequency different than the other two windings. Accordingly, the cube-shaped marker 58 is also a wireless, three-axis, resonating marker.

In one embodiment, the wireless, excitable markers 30 are configured to resonate and provide a measurable signal within the frequency range of approximately 10kHz to 200kHz, inclusive. In other embodiments, the markers 30 can be self-contained, powered markers that include a power source, such as a battery, that provides sufficient power to produce the measurable identifiable marker signal. In other embodiments, the markers 30 can be "wired" markers connectable via wires to a selected power or excitation source to allow the markers to generate the unique marker signal. The marker signal can be unique as a function of frequency (i.e., frequency multiplexing) as a function of time or time multiplexing.

In selected applications, a single marker 31, preferably a single-axis marker, is implanted in the target 12, and the intensity of the signals from the single resonating marker is used to determine the target location information relative to the sensor array 34. In alternate embodiments, two, three, or more markers 30 are implanted at known locations in or adjacent to the target. Each marker 30 produces its unique signal relative to the other markers, so the sensor array 34 differentiates between the markers by frequency multiplexing. The sensor array 34 measures the intensity of the unique signals from the markers 30. The signal intensity measurements are converted for use in geometric calculations (discussed in greater detail below) to accurately determine the actual three-dimensional location (X, Y, Z) and possibly the angular orientation (pitch, yaw, roll) of the marker relative to the sensor array 34.

Referring again to FIG. 8, the system 10 includes the excitation source 32 that generates a magnetic field for exciting the markers 30. The excitation source is positioned in a selected location relative to the target 12 and close enough to the markers 30 so the emitted magnetic field has sufficient intensity to acceptably energize the markers. In the illustrated embodiment, a plurality of markers 30 are permanently implanted within the patient's body 14 in or adjacent to the target 12. In one embodiment, the computer controller 38 provides a separate driver circuit for the excitation source 32 for each marker 30, so as to selectively excite the respective marker at the selected frequency. The excitation source 32 in one embodiment is a three-dimensional, AC magnetic field source that generates three-dimensional magnetic fields in the X, Y, and Z axes. This excitation source 32 provides one source coil for each marker 30, and the electric current driven through the source coil generates the AC magnetic waveform tuned for the respective markers. In another embodiment, the source coil (or coils) in the excitation source 32 is provided by a coil configured to generate the multiple or scanned excitation frequency fields for the respective markers 30.

Figure 13:
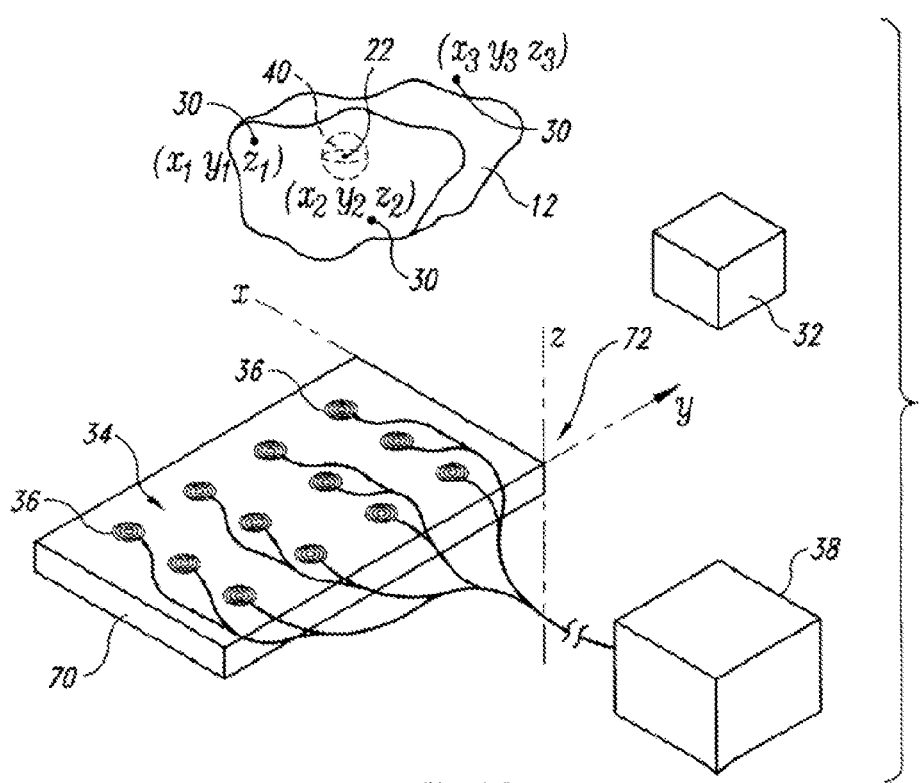
FIG. 13 and FIG. 14 are schematic isometric views of sensor arrays.
Figure 14:
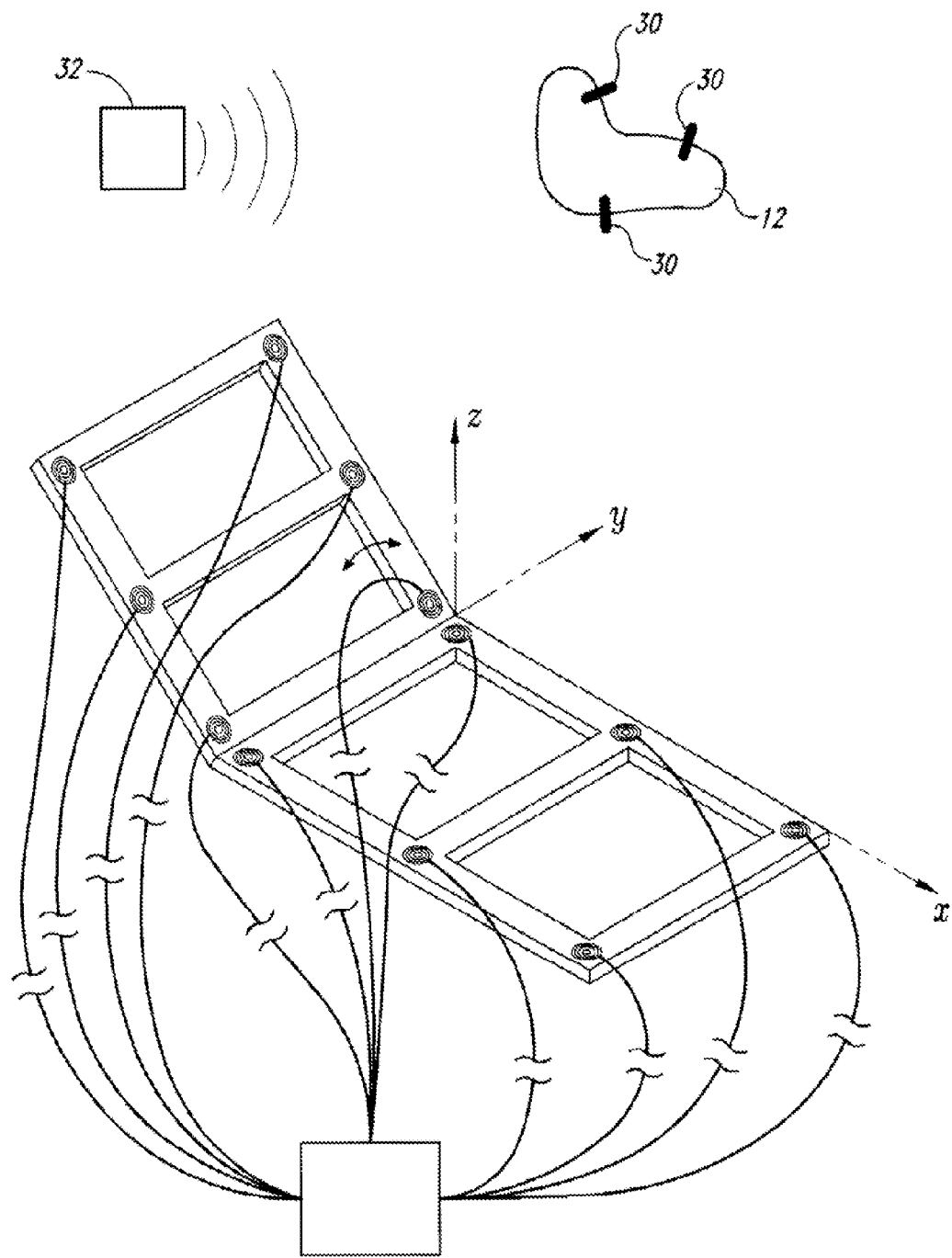

FIGS. 13 and 14 are schematic isometric views of sensor arrays 34 positionable exterior of the body (FIG. 13) and spaced apart from the markers 30 positioned in or near the target 12. In these illustrated embodiments, three markers 30 are shown implanted in or near the target 12. As seen in FIG. 13, the sensor array 34 includes a frame 70 that supports a plurality of sensors 36 in a fixed and known geometry relative to each other along X, Y, or Z axes of a reference coordinate system 72. The position of each sensor 36 on the frame 70 relative to the reference coordinate system 72 is fixed and defines fixed reference points for obtaining measurement data used by the computer controller 38. In the embodiment of FIG. 13, the frame 70 supports the sensors 36 so the sensors are positioned in a single plane. In the embodiment of FIG. 14, the frame 70 is shaped to support the sensors 36 in two orthogonal planes, so the sensors 36 are oriented along the X, Y, and Z axes of the reference coordinate system 72. Accordingly, the sensor array 34 provides the fixed reference structure from which measurements are taken and calculations performed to determine the relative positions of the target 12, the target isocenter 40 and the machine isocenter 22.

The illustrated embodiments of FIGS. 13 and 14 utilize "wireless" markers 30, so frequency multiplexing is utilized to distinguish the signals from the different markers. Each sensor 36 is a three-axis sensor that measures the absolute marker signal strengths from a respective one of the markers 30 relative to the X, Y, and Z axes. The absolute signal strength of the marker signal along each axis in the reference coordinate system 72 is measured by the sensors 36 for each marker in order to determine the X, Y, and Z position of each marker.

It is known that the strength of a magnetic field decreases at a ratio proportional to the cube of the distance from the source. Accordingly, the distance of the marker from the sensor can be determined based upon the marker's signal strength. The geometric relationship from the marker to a series of sensors that are spaced at known locations relative to each other is used to solve a series of equations with one unique result. Accordingly, the distance between the marker 30 and the sensor 36 calculated by the computer controller 38 based on the marker's signal strength measured by the respective sensors and iterated for a best fit solution to the geometric equations.

The precise location of a marker 30 in space relative to the sensor array 34 can be calculated based upon the distances between that marker and at least four separate three-axis sensors spaced apart from each other in the array. The absolute magnitude of the distance from the three-axis sensor is determined by squaring the each of the three axis magnitudes (x, y, and z orientations), adding the results and finally taking the square root for the distance resultant. As an example, the distance between one sensor 36 and one of the markers 30 corresponds geometrically to the radius of a sphere.

Figure 15:
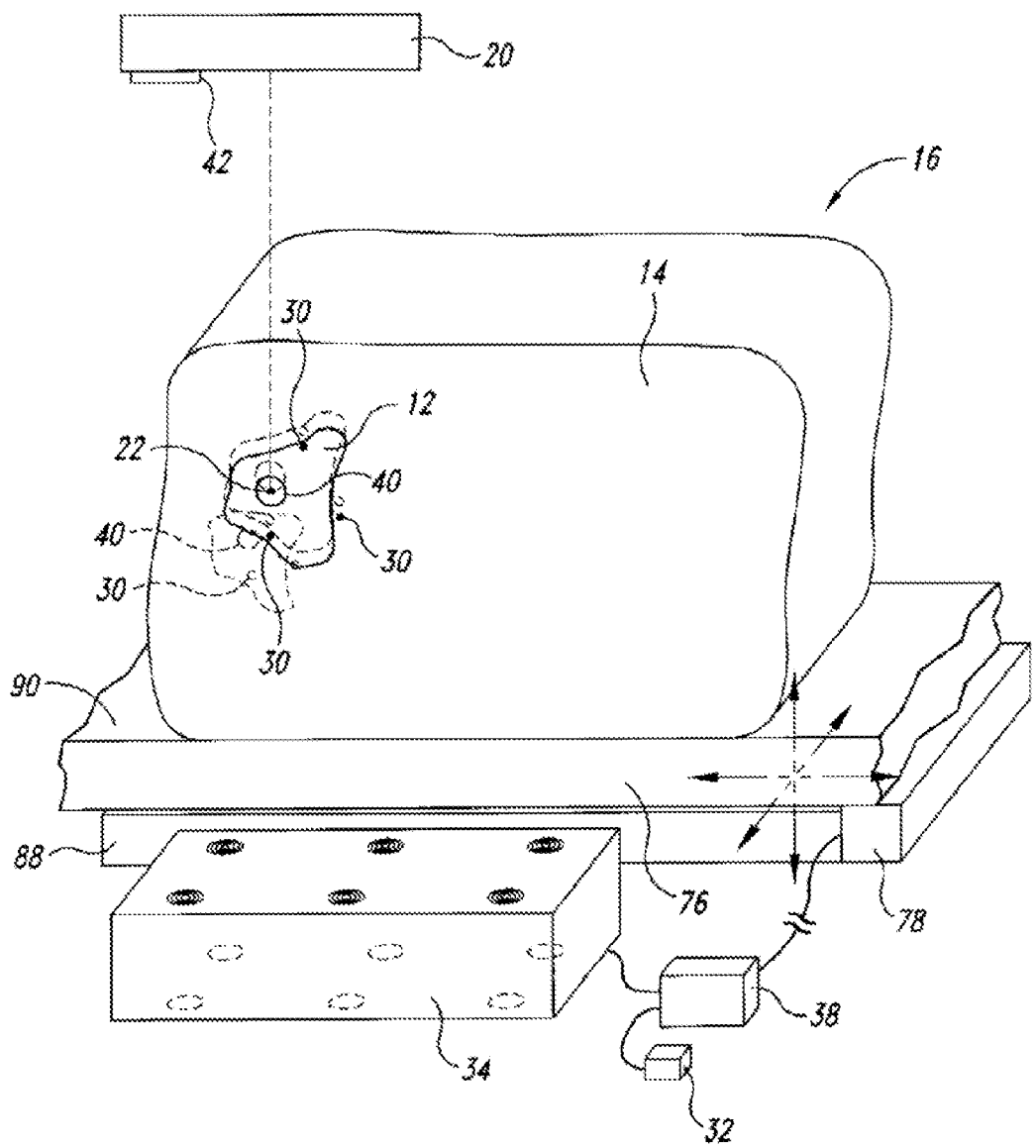
FIG. 15 is a partial isometric view of a support table that movably supports a patient's body.

FIG. 15 is a partial isometric view illustrating an aspect of the present invention that includes a support table 76 that movably supports the patient's body 14 under the gantry 20 and adjacent to the sensor array 34. The support table 76 is positionable below the machine isocenter 22. The support table 76 is movable to adjust the position of the patient 16 relative to the machine isocenter 22 until the target isocenter 40 is coincident with the machine isocenter. The sensor array 34 may be placed on, under, or connected to the support table 76. Alternatively, it may be mounted to the linear accelerator's gantry at a location sufficiently close to any markers 30 (implanted, external or gantry) that are to be located. In this alternate embodiment with the sensor array 34 mounted to the linear accelerator, the position from the machine isocenter 22 to the sensor array will be known, so that a separate gantry marker 42 may not be used.

As best seen in FIGS. 8 and 15, the support table 76 has a base 88 and a tabletop 90 movably supported to the base for linear and angular movement relative to the sensor array 34. A movement control system 78 is connected to the tabletop 90 to control movement of the tabletop and the patient 16 relative to the machine isocenter 22 and the sensor array 34. The control system 78 is also coupled to the computer controller 38, and the computer controller 38 is programmed to activate the control system 78 to adjust the linear or angular position of the patient. In one embodiment, the tabletop's position moves in response to an authorized user such as doctor, physicist or technician activating the control system, or automatically in response to instructions provided by the computer controller 38.

Once the target 12 is positioned so the target isocenter 40 is coincident with the machine isocenter 22, ionizing radiation can be selectively and very accurately delivered directly to the target area or volume. Application of the radiation therapy to the target 12, can be provided at the selected dosage and intensity with precise accuracy, while potentially minimizing the margin needed around the target. In one embodiment, the actual position of the target isocenter 40 is substantially continuously monitored and tracked relative to the machine isocenter 22 during delivery of the radiation therapy. If the target isocenter 40 moves away from the machine isocenter 22 beyond an acceptable range of displacement distances, the computer controller 38 provides a signal to the radiation delivery device to interrupt the radiation therapy to the target. The target's position can then be adjusted manually or automatically until the target isocenter 40 is again coincident with the machine isocenter 22, and radiation therapy can resume. In one embodiment, the computer controller 38 is programmed so that if the target isocenter 40 moves from the machine isocenter 22, but the distance of movement does not exceed the acceptable range, the computer controller 38 will not interrupt the radiation therapy. This range of movement is dependent upon many factors, such as the target type (e.g., prostate, lung, liver), target size, target location, beam shape/size, and the radiation treatment plan.

Figure 16:
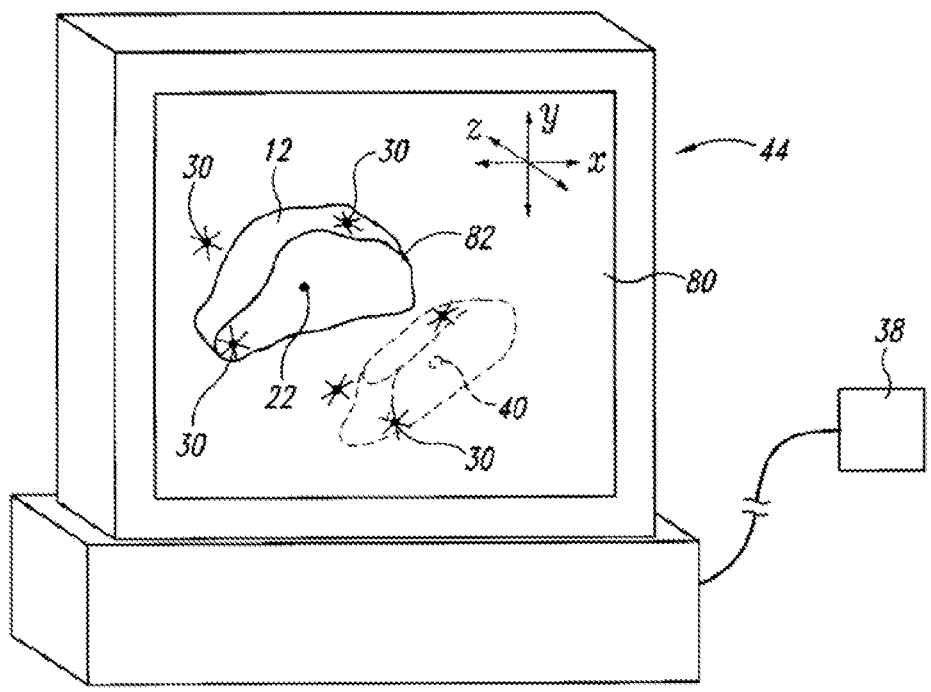
FIG. 16 and FIG. 17 illustrate a feedback portion of a monitoring assembly that provides feedback data to an operator.
Figure 17:
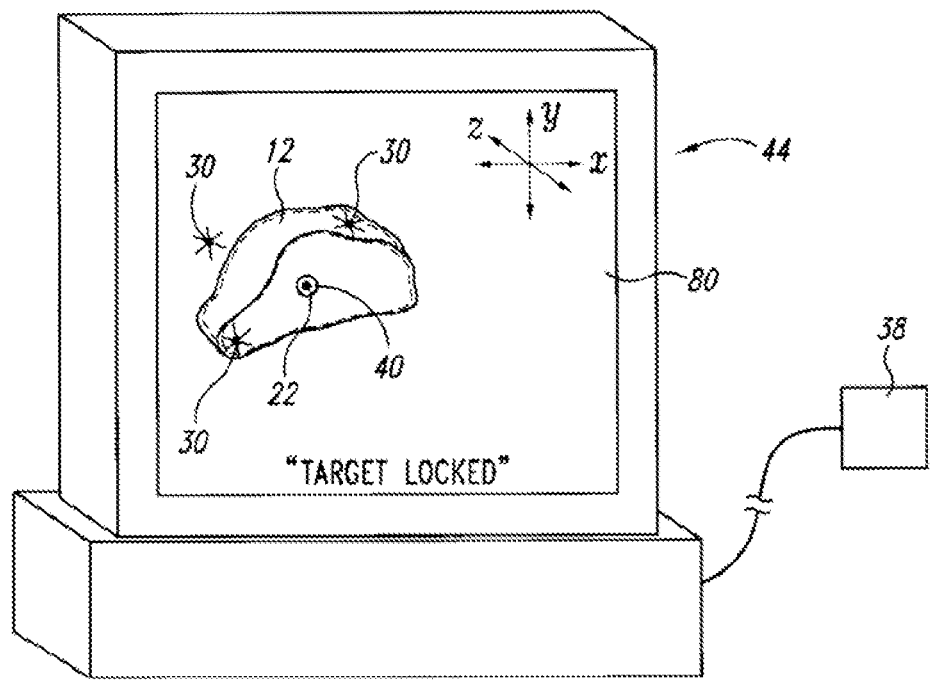

Tracking of the target isocenter's position is facilitated by the monitoring assembly 44, which is coupled to the computer controller 38. FIGS. 16 and 17 illustrate a feedback portion 80 of the monitoring assembly 44 that provides feedback data to an operator about, as an example, the position of the markers 30, the target isocenter 40 and the machine isocenter 22. The feedback portion 80 is a display monitor that provides pictorial, graphical, or textual information to the operator. Other feedback portions 80, such as graphical display devices, auditory feedback devices, or visual feedback devices can be used in alternate embodiments. In one embodiment, the computer controller 38 contains imaging data, such as from a CT, MRI, or ultrasound imaging system that defines the shape and size of the target 12 within the body 14. The imaging data also defines the locations of each marker 30 in or around the target 12. The computer controller 38 uses the imaging data to provide a simulated model of the target, the markers, and the target isocenter. This simulated model is displayed on the feedback portion 80 as shown in FIG. 16 in phantom lines. The simulated model is also displayed overlaying the machine isocenter 22, so the simulated target isocenter 40 is coincident with the machine isocenter. The simulated target and simulated markers can also display how the actual target needs to be positioned and oriented three-dimensionally for the particular radiation therapy to be applied to the target.

The monitoring assembly 44 also receives and displays information from the computer controller 38 to show the actual locations of the markers 30 and target isocenter 40 relative to the machine isocenter 22, and relative to the simulated target and markers. Accordingly, the feedback portion 80 allows the operator to determine the actual position of the markers relative to the simulated markers, and the target isocenter 40 relative to the machine isocenter 22 substantially in real time while the patient 16 is on the support table 76 (FIG. 8). The patient 16 and support table 76 can be repositioned until the target 12 is properly oriented for the selected radiation therapy.

Figure 18:
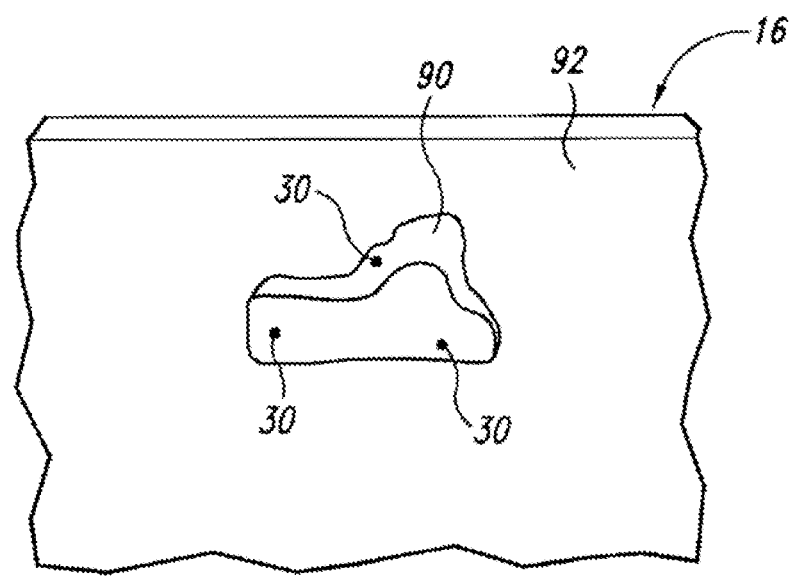
FIG. 18 and FIG. 19 are schematic views showing a tumor in a body.
Figure 19:
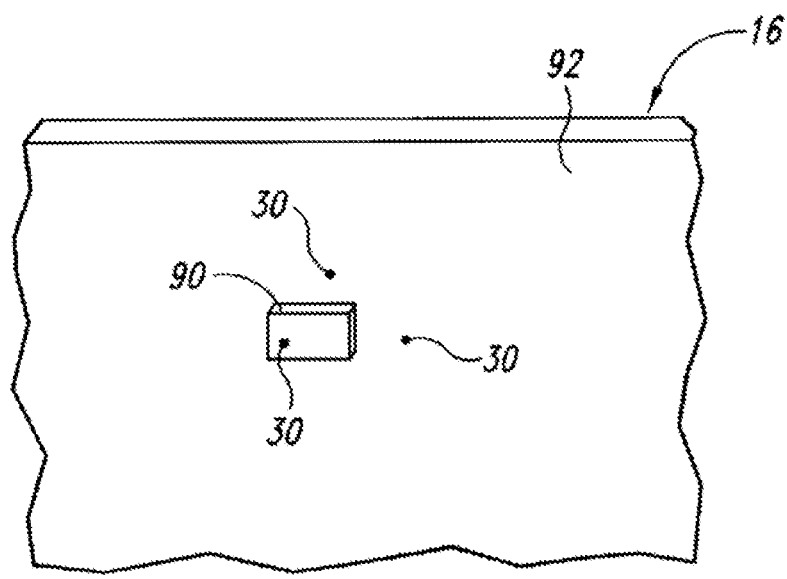
Figure 20:
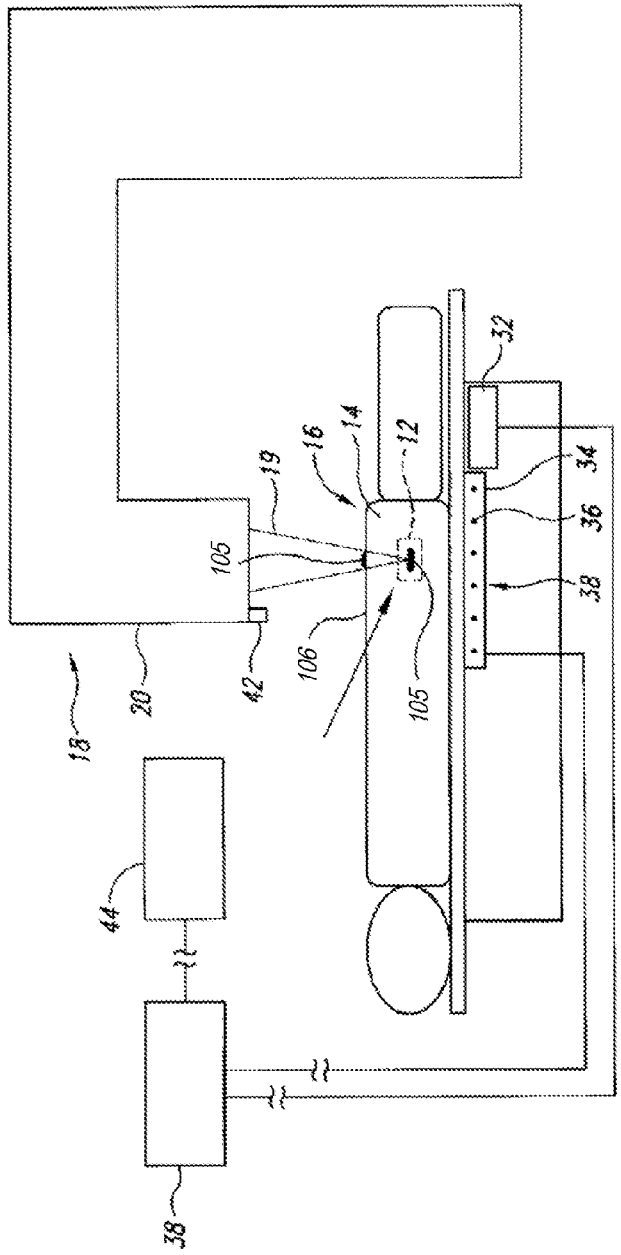
FIG. 20 and FIG. 21 illustrate surface-mounted markers adhered to the exterior surface of a patient's body.
Figure 21:
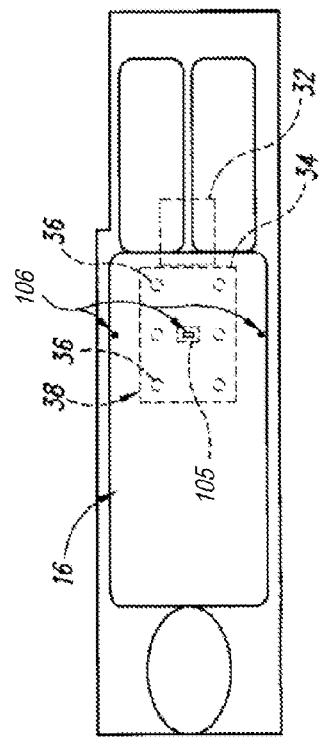
Figure 22:
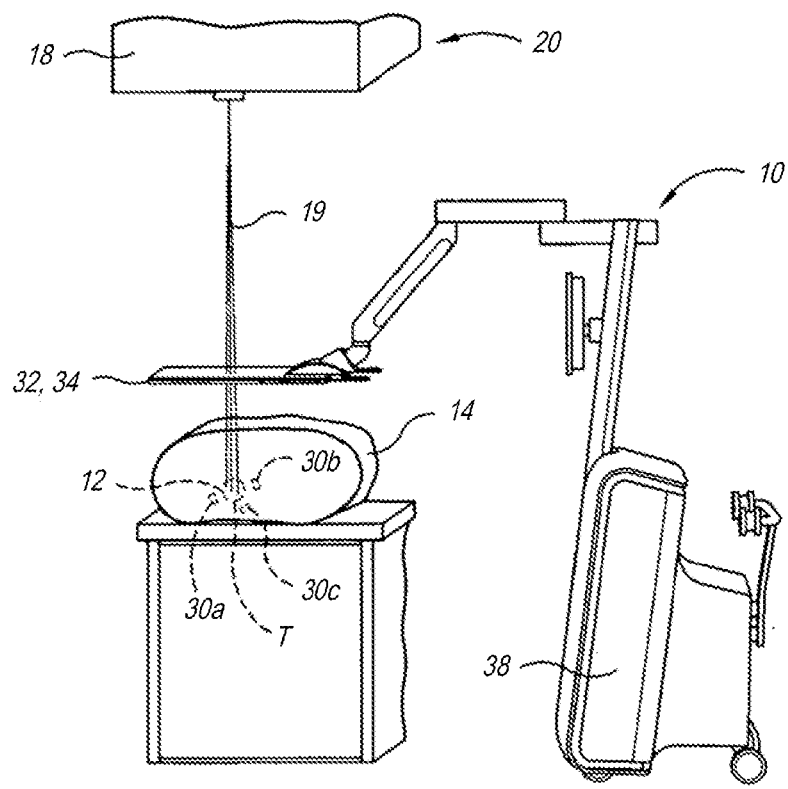
FIG. 22 is a side elevation view of a tracking system for use in localizing and monitoring a target in accordance with an embodiment of the present invention. Excitable markers are shown implanted in or adjacent to a target in the patient.
Figure 23:
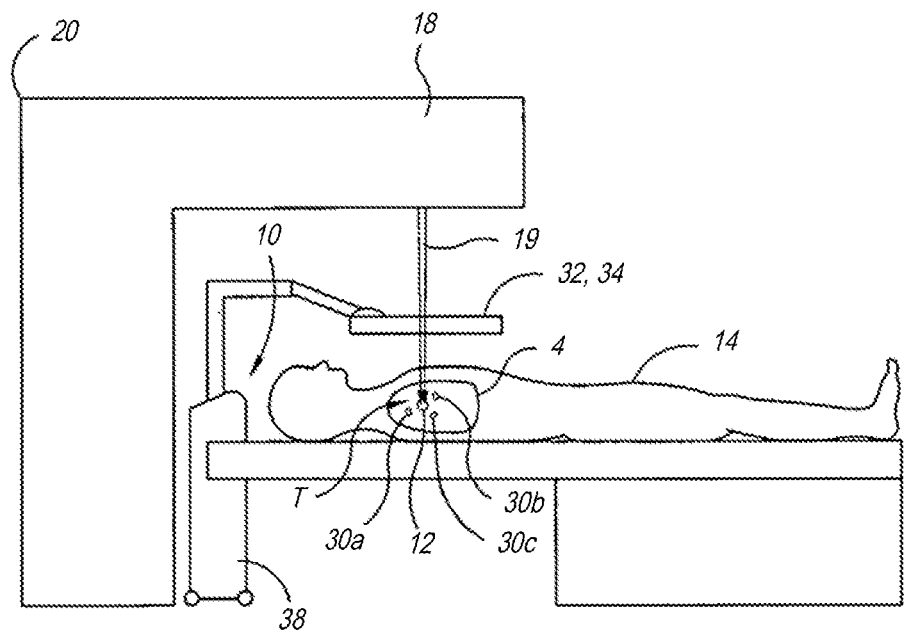
FIG. 23 is a schematic elevation view of the patient on a movable support table and of markers implanted in the patient.

In addition to accurately tracking and monitoring the position of the target 12 relative to the machine isocenter 22, the system 10 is also usable to monitor the status of the target, such as a tumor or the like, in a patient's body 14 over time. FIGS. 18 and 19 are schematic views showing a tumor 90 in a body 92. Three markers 30 are shown for this embodiment permanently implanted in or adjacent to the tumor 90. Images of the tumor 90 and markers 30 are obtained by CT, MRI, ultrasound, or other imaging technique over time. From these multiple images of the tumor 90 and markers 30, the position of the markers relative to the tumor can be compared and tracked. Accordingly, a doctor can use the markers 30 in the multiple images as a reference tool to determine whether the tumor has shrunk, grown, moved, or otherwise changed within the patient's body.

As an example, FIG. 18 illustrates an image of a tumor 90 in a first condition with three markers 30 implanted therein, and FIG. 19 illustrates a second image of the tumor taken later in time. The second image shows the same markers 30 in the same location within the patient's body, and from the position of the tumor relative to the markers, one can see that the tumor has shrunk. Thus, doctors can track the status of tumors or other targets within the body over time to determine, as an example, the effectiveness of radiation therapy, whether additional treatments are needed, or whether a change in tumor growth has occurred or whether the radiation treatment plan needs to be altered.

In the embodiments discussed above, the markers 30 are described and shown as being subcutaneously implanted in or next to a target 12. This implantation of the markers 30 is performed when needed to ensure that, if the target 12 moves, the markers will move with the target as a unit. In an alternate embodiment illustrated in FIGS. 20 and 21, the markers are surface-mounted markers 105 adhered to the exterior surface 106 of the patient's body 14 substantially adjacent to and in alignment with a target 12, in or on the body. The surface-mounted markers 105 can be removably adhered with an adhesive, such as tape or the like, in a substantially fixed location on the body's exterior surface 106 relative to the target 12. These surface-mounted markers 105 are particularly suitable for targets 12 known not to substantially move within the body 14 relative to the exterior surface. The surface-mounted markers 30 are also suitable for use when the target's size or location in the body 14 is such that some motion of the target isocenter is not critical for effective radiation therapy or treatment. Accordingly, the surface-mounted markers 105 provide reference points for accurate alignment and orientation of the target 12 and the machine isocenter 22. Alternatively, markers 30 may be mounted on or in patient immobilization devices at known locations relative to the treatment isocenter.

The surface-mounted markers 105 in one embodiment are wireless markers, so that the markers can remain adhered on the patient's body 14 after a radiation treatment session so that the patient 16 can come and go from the treatment area without disrupting the position of the markers 105 relative to the target 12. In alternate embodiments, the markers 105 remain adhered to the patient 16 and are connectable to lead wires of a "wired" marker system in the treatment area. The lead wires can be disconnected from the markers 105 to allow the patient 16, to leave the treatment area while the markers remain fixed in place on the patient's body.

The surface-mounted markers 105 are also usable to monitor a patient's base-line girth (anterior-posterior and lateral dimensions) during a radiation treatment program. The baseline girth measurements, referred to as patient separations, are initially obtained by CT, MRI, or physical measurements. Patient separations are used when preparing a radiation treatment plan for the patient. The surface-mounted markers 105 can be utilized alone or in combination with implanted markers to provide data about changes in the patient separations that may occur during chemo or radiotherapy. Each surface-mounted marker 105 has an identifiable initial position in space relative to, as an example, the target isocenter or relative to each other. The sensor array 34 and computer controller 38 are configured to determine the distances between each surface-mounted marker and/or the target isocenter. The computer controller 38 calculates and monitors the distances, corresponding to the patient separations. During the course of radiation treatment, if the patient separations change significantly, such as due to substantial weight loss from chemo or radiotherapy, the treatment plan may become invalid because less patient tissue is available to alternate the radiation beam, thereby resulting in higher than planned doses of radiation.

In one embodiment, the surface-mounted markers 105 are usable to facilitate and speed up patient set-up procedures before and/or during the radiation therapy procedure. The surface mounted markers 105 are positioned at selected locations on the patient's body 14 at known positions. The markers 105 are excited and the locations relative to the sensor array are determined. The marker's location information can then be used to calculate the Target Skin Distance or Source Skin Distance, which is the distance between the exterior skin of the patient and the linear actuator or the tabletop. The markers 105 can also be used to determine the tabletop-to-isocenter, which is the distance between the tabletop to the marker or other alignment means, such as laser cross-hairs projected on to the patient's skin. Accordingly, the surface mounted markers 105 can be used to automatically calculate the relevant distances during the set up procedure to quickly determine if the patient is properly positioned in accordance with the radiation therapy treatment plan.

In another embodiment, the surface-mounted markers 105 can be used in conjunction with one or more markers 30 implanted in or near the target 12. The relative location of each marker 105 or 30 can be calculated and used for any combination of patient set-up, target locating, target positioning, target motion tracking, and/or target evaluation, as discussed above.

It will be appreciated by those skilled in the art that the above-described facility may be straightforwardly adapted or extended in various ways. For example, the facility may operate in a wide variety of radiation treatment and treatment planning environments. The facility can exchange positioning data containing various elements, in various formats, via various storage or communications media. The facility can use a wide variety of treatment planning processes to incorporate the positioning data in future treatment plans. In preparing treatment plans, the facility can use positioning data from any number of prior sessions to prepare plans for any number of future sessions. In some cases, the facility adapts the treatment plan for a session during the course of the session, and delivers radiation therapy in accordance with the adapted plan. While the foregoing description makes reference to preferred embodiments, the scope of the invention is defined solely by the claims that follow and the elements recited therein.

We claim:

1. A method in a computing system for facilitating custom radiation treatment planning, comprising:
    during a first radiation treatment session associated with a first treatment plan
        determing locations of a plurality of markers implanted in a patient's body using non-ionizing radiation, and
        collecting data indicating positioning of a predefined treatment site of the patient relative to a target treatment location based on the determined locations throughout the first radiation treatment session;
    associating the collected positioning data with data describing a plurality of radiation treatment fields used during the first radiation treatment session;
    providing at least the associated data to a treatment planning facility to determine a second treatment plan for a future radiation treatment session for the patient to be performed on a different date than the first treatment plan and over a period of time; and
    producing the second treatment plan by
        comparing intended positioning data of the first treatment plan with the collected positioning data throughout the first radition treatment session, and
        modifying the first treatment plan based on the comparison of the intended positioning data with the collected positioning data.

2. The method of claim 1, further comprising associating at least a portion of the collected positioning data with other data of the first treatment plan.

3. The method of claim 1, further comprising associating at least a portion of the collected positioning data positioning data with other data stored in a record and verify system.

4. The method of claim 1 further comprising, before providing the associated data to the treatment planning facility, discarding portions of the associated data corresponding to time periods during which radiation was not delivered to the patient.

5. The method of claim 1 wherein the collected data indicates a vector between the target treatment location and the predefined treatment site of the patient.

6. The method of claim 1 wherein the collected data indicates an orientation of the patient relative to a source of radiation treatment.

7. The method of claim 1 wherein the associated data provided to the treatment planning facility is provided as a time series.

8. The method of claim 1 wherein producing the second treatment plan further includes accounting for deformations in the predefined treatment site due to real-time changes or day-to-day changes.

9. The method of claim 1 wherein the associated data comprises information related to the healthy tissue surrounding the target treatment location.

10. The method of claim 1 wherein producing the second treatment plan further includes estimating and/or inferring information related to bone or tissue that does not contain markers or fiducials.

11. The method of claim 1 wherein the associated data provided to the treatment planning facility further comprises data indicating, throughout the radiation treatment session, a measure of the rate at which radiation energy is delivered.

12. The method of claim 1 wherein the associated data provided to the treatment planing facility further comprises data indicating, throughout the radiation treatment session, a cross-sectional shape of a radiation beam in which radiation energy is delivered.

13. The method of claim 1 wherein the associated data provided to the treatment planning facility further comprises data indicating, throughout the radiation treatment session, a direction of a radiation beam in which radiation energy is delivered.

14. A method in a computing system for facilitating custom radiation treatment planning using a plurality of markers implanted in a patient's body proximate a target treatment location, the method comprising:
during a first radiation treatment session for a patient, determining locations of the markers using non-ionizing radiation and collecting data indicating positioning of a predefined treatment site of the patient relative to the target treatment location throughout the first radition treatment session, wherein the first radiation treatment session is associated with a first treatment plan that includes data indicating intended positioning through the first radiation treatment session of the predefined treatment site of the patient relative to the target treatment location;
associating the collected positioning data with data describing a plurality of radiation treatment fields used during the first radiation treatment session;
comparing intended positioning data of the first treatment plan with the collected positioning data throughout the first radiation treatment session; and
providing at least the associated data to a treatment planning processor to determine a second treatment plan for a future radiation treatment session for the patient to be performed on a different date than the first treatment plan, wherein the second treatment plan is a modification of the first treatment plan based at least in part on the comparison of the collected positioning data with the intended positioning throughout the first radiation treatment session.

15. The method of claim 14 wherein the collected positioning data is first collected positioning data, the associated data is first associated data, and the future radiation treatment session is a first future radiation treatment session, and wherein the method further comprises:
during the first future radiation treatment session, determining locations of the markers using non-ionizing radiation and collecting corresponding positioning data to produce second collected positioning data;
associating the second collected positioning data with data describing a plurality of radiation treatment fields used during the first future radiation treatment session to produce second associated data;
comparing intended positioning data of the second treatment plan with the second collected positioning data; and
providing at least the second associated data to the treatment planning processor to determine a third treatment plan for a second future radiation treatment session for the patient to be performed at a later date than the first future radiation treatment session, wherein the third treatment plan is a modification of at least the second treatment plan based at least in part on the comparison of the second collected positioning data with the intended positioning throughout the first future radiation treatment session.

16. The method of claim 14 wherein associating and comparing the collected positioning data is carried out at least in part with a patient tracking system, and wherein the method further comprises providing the associated data from the patient tracking system to a treatment planning facility.

17. The method of claim 14 further comprising determining a direction in which radiation is to be delivered to the patient throughout the second radiation treatment session based at least on the associated data.

18. The method of claim 14 further comprising determining a cross-sectional shape of a radiation beam by which radiation energy is to be delivered to the patient during the second radiation treatment session based at least in part on the associated data.

19. A system for facilitating custom radiation treatment planning using a plurality of markers implanted in a patient's body proximate a target treatment location, the system comprising:
a first subsystem configured to
determine locations of each of the markers during a first radiation treatment session using non-ionizing radiation,
collect data indicating a position of a predefined treatment site relative to the target treatment location based on the determined locations throughout the first radiation treatment session;
associate the collected positioning data with data describing a plurality of radiation treatment fields used during the first radiation treatment session; and
provide at least the associated data to a second subsystem,
wherein the second subsystem is configured to determine a second treatment plan for a future radiation treatment session for the patient to be performed on a different date than the first treatment plan, and wherein the second treatment plan is a modification of the first treatment plan based at least in part on a comparison of the collected positioning data with the intended positioning throughout the first radiation treatment session.

20. The system of claim 19 wherein the second subsystem is associated with a treatment planning facility to which the first subsystem provides the associated data.

* * * * *